United States Patent

Ando et al.

[11] Patent Number: 5,814,648
[45] Date of Patent: Sep. 29, 1998

[54] N-HYDROXYUREAS AS ANTIINFLAMMATORY AGENTS

[75] Inventors: Akemi Ando, Taketoyo-cho; Rodney William Stevens, Handa, both of Japan

[73] Assignee: Pfizer Inc., New York, N.Y.

[21] Appl. No.: 945,671

[22] PCT Filed: Jun. 7, 1995

[86] PCT No.: PCT/JP95/01127

§ 371 Date: Nov. 5, 1997

§ 102(e) Date: Nov. 5, 1997

[87] PCT Pub. No.: WO96/40659

PCT Pub. Date: Dec. 19, 1996

[51] Int. Cl.$^6$ .......... A61K 31/42; A61K 31/425; A61K 31/44; C07D 263/14
[52] U.S. Cl. .......... 514/374; 548/146; 548/238; 546/270.4; 546/271.4; 514/340; 514/365
[58] Field of Search ............. 548/146, 238; 546/270.4, 271.4; 514/340, 365, 374

[56] References Cited

U.S. PATENT DOCUMENTS 5,288,751  2/1994  Brooks et al. .......... 514/438

5,464,849  11/1995  Mano et al. .......... 514/365

FOREIGN PATENT DOCUMENTS

WO92/01682  2/1992  WIPO .
WO92/22543  12/1992  WIPO .
WO94/22814  10/1994  WIPO .

*Primary Examiner*—Laura L. Stockton
*Attorney, Agent, or Firm*—Peter C. Richardson; Paul H. Ginsburg; Jolene W. Appleman

[57] ABSTRACT

Described herein are N-hydroxyurea compounds having the ability to inhibit the 5-lipoxygenase enzyme and having formula (I) and the pharmaceutically acceptable salts thereof. The variables are described herein. These compounds are useful in the treatment or alleviation of inflammatory diseases, allergy and cardiovascular diseases in mammals and as the active ingredient in pharmaceutical compositions for treating such conditions.

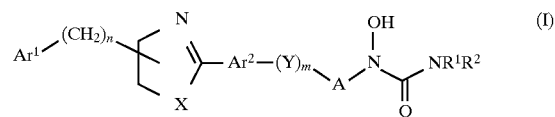

11 Claims, No Drawings

N-HYDROXYUREAS AS ANTIINFLAMMATORY AGENTS

This application is a 371 of PCT/JP95/01127 filed Jun. 7, 1995.

TECHNICAL FIELD

This invention relates to novel N-hydroxyurea compounds. The compounds of the present invention inhibit the action of the lipoxygenase enzyme and are useful in the treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase A2. Arachidonic acid is then metabolized either by cyclooxygenase to produce the prostaglandins and thromboxanes or by lipoxygenase to generate hydroperoxy fatty acids which may be further metabolized to the leukotrienes. Leukotrienes have been implicated in the pathophysiology of inflammatory diseases, including rheumatoid arthritis, gout, asthma, ischemia reperfusion injury, psoriasis and inflammatory bowel diseases and are the subject of several review articles. Any drug that inhibits lipoxygenase is expected to provide significant new therapy for both acute and chronic inflammatory conditions. (See H. Masamune and L. S. Melvin, Sr., Annual Reports in Medicinal Chemistry: 24 (1989) pp71–80 (Academic), B. J. Fitzsimmons and J. Rokach, Leukotrienes and Lipoxygenases (1989) pp427–502 (Elsevier)) and D. G. Batt, Progress in Med. Chem.29 (1992) p 1.

WO 92/22543(1992) discloses N-hydroxyurea and hydroxamic acid compounds as inhibitors of the lipoxygenase enzyme.

BRIEF DISCLOSURE OF THE INVENTION

The present invention provides novel N-hydroxyurea compounds of the following chemical formula (I):

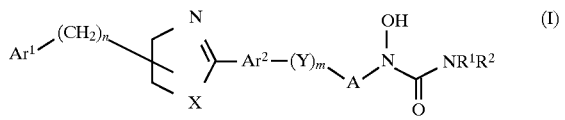

and the pharmaceutically acceptable salts thereof, wherein A is $C_1$–$C_4$ alkylene, CH(R), CH(R)CH$_2$ or CH(R)CH$_2$CH$_2$, in which R is methyl or ethyl; m and n are each zero or one; $R^1$ and $R^2$ are each hydrogen, $C_1$–$C_4$ alkyl or $C_2$–$C_6$ alkenyl; X is O or S; Y is O, S, CH=CH or C≡C; $Ar^1$ is phenyl or phenyl mono-substituted with halogen, $C_1$–$C_4$ alkyl, $C_1$–$C_4$ alkoxy, $C_1$–$C_4$ halo-substituted alkyl or $C_1$–$C_4$ halo-substituted alkoxy; and $Ar^2$ is phenylene, pyridylene or phenylene mono- or di-substituted with halogen, $C_1$–$C_4$ alkyl, $C_1$–$C_4$ alkoxy, $C_1$–$C_4$ halo-substituted alkyl or $C_1$–$C_4$ halo-substituted alkoxy.

The compounds of the formula (I) inhibit the 5-lipoxygenase enzyme. Therefore the compounds are useful for treating a medical condition for which a 5-lipoxygenase inhibitor is needed, in a mammalian subject, e.g., a human subject. The compounds are especially useful for treating allergic and inflammatory conditions. This invention also embraces pharmaceutical compositions which comprise a compound of the formula (I) and a pharmaceutically acceptable carrier.

A preferred group of compounds of the invention consists of the compounds of the formula (I), wherein n is zero; $R^1$ and $R^2$ are each hydrogen; X is O; $Ar^1$ is phenyl or 4-fluorophenyl; and $Ar^2$ is 1,3-phenylene or 1,3-phenylene having one substituent selected from halogen, $C_1$–$C_4$ alkyl, $C_1$–$C_4$ alkoxy, $C_1$–$C_4$ halo-substituted alkyl and $C_1$–$C_4$ halo-substituted alkoxy.

Within this preferred group, a particularly preferred subgroup of compounds are those wherein A is CH$_2$, CH$_2$CH$_2$, CH(CH$_3$) or CH(CH$_3$)CH$_2$; $Ar^2$ is 1,3-phenylene or 1,3-phenylene having one fluoro substituent; m is one; and Y is O. Within this particularly preferred subgroup, $Ar^1$ is preferably attached to the 4-position of the oxazoline ring, and the carbon atom to which $Ar^1$ is attached preferably has the (R)-configuration.

Particularly preferred individual compounds of the invention are:

(+)-N-[3-[3-(4,5-Dihydro-4(R)-phenyloxazol-2-yl)phenyl]-2-propyn-1-yl]-N-hydroxy-N'-methylurea;

(+)-N-[3-[3-[4,5-Dihydro-4(R)-(4-fluorophenyl)oxazol-2-yl]phenyl]-2-propyn-1-yl]-N-hydroxyurea;

(-)-N-[3-[3-(4,5-Dihydro-4(R)-phenyloxazol-2-yl)-2-fluorophenyl]-2-propyn-1-yl]-N-hydroxyurea;

N-[4-[3-(4,5-Dihydro-5-phenyloxazol-2-yl)phenyl]-3-butyn-2-yl]-N-hydroxyurea;

(-)-N-1-[2-[3-(4,5-Dihydro-(4R)-phenyloxazol-2-yl)phenoxy]ethyl]-N-hydroxyurea;

(+)-N-1-[2-[3-(4,5-Dihydro-4(R)-phenyloxazol-2-yl)-5-fluorophenoxy]ethyl]-N-hydroxyurea; and N-1-[2-[3-[4,5-Dihydro-4(R)-phenyloxazol-2-yl]-2-fluorophenoxy]ethyl]-N-hydroxyurea.

DETAILED DISCLOSURE OF THE INVENTION

In this application, the term "halo" is used to mean radicals derived from the elements fluorine, chlorine, bromine or iodine.

The term "pharmaceutically acceptable salts" refers to (1) the base salts of the compound of this invention containing non-toxic cations, including, but not limited to, cations based on the alkali and alkaline earth metals, such as sodium, lithium, potassium, magnesium, and the like, as well as non-toxic ammonium, substituted ammonium and quaternary ammonium cations, including, but not limited to, ammonium, tetramethylammonium, tetraethylammonium, methylammonium, diethylammonium, trimethylammonium, triethylammonium and the like, or refers to (2) the acid addition salts of the compound of this invention containing non-toxic acids, including, but not limited to, hydrochloride, sulfate or bisulfate, phosphate or acid phosphate, acetate, fumarate, glutconate, lactate, maleate, succinate, tartrate, methanesulfonate, benzenesulfonate, toluenesulfonate and formate salts.

The term "halo-substituted alkyl" refers to an alkyl radical substituted with one or more halogens including, but not limited to, chloromethyl, 1-fluoroethyl, trifluoromethyl and the like. The preferred halo-substituted alkyl group is trifluoromethyl.

The term "halo-substituted alkoxy" is used to mean an alkoxy radical substituted with one or more halogens including, but not limited to, chloromethoxy, 2-chloroethoxy, difluoromethoxy, trifluoromethoxy and the like. The preferred halo-substituted alkoxy group is trifluoromethoxy.

The novel hydroxyureas of formula (I) may be prepared by a number of synthetic methods that are well known by those skilled in the art.

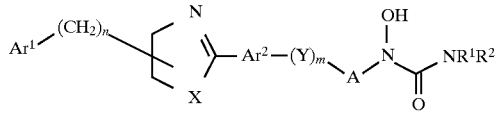

In one embodiment, compounds of the formula (I) are prepared according to the reaction step outlined in scheme 1.

Scheme 1

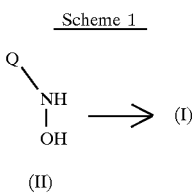

In the above scheme, Q is

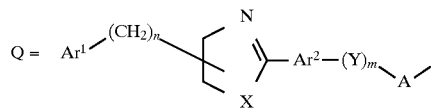

and $R^1$, $R^2$, $Ar^1$, $Ar^2$, X, Y, A, n and m are as previously defined.

In the reaction step in scheme 1, the compounds (I) are obtained by treating the hydroxylamine (II) with a trialkylsilyl isocyanate, such as trimethylsilyl isocyanate, or an alkyl or alkenyl isocyanate of the formula $R^6$—N=C=O in a reaction-inert solvent. Suitable solvents that do not react with reactants and/or products are, for example, tetrahydrofuran (THF), dioxane, dichloromethane ($CH_2Cl_2$) or benzene. The range of preferable temperature is from ambient temperature to the reflux temperature of the solvent, e.g. 15° to 80° C., but if necessary, temperatures lower or higher can be adopted. The reaction is easily monitored by thin-layer chromatography (TLC) techniques. The reaction time is in general from a few minutes to several hours.

An alternative procedure employs treatment of (II) with gaseous hydrogen chloride in a reaction-inert solvent such as benzene or toluene and then subsequent treatment with phosgene. Reaction temperatures are usually in the range of ambient temperature through to boiling point of solvent, e.g. 15° to 100° C., but if necessary, temperatures lower or higher can be adopted. The intermediate chloroformamide is not isolated but subject to (i.e. in situ ) reaction with an appropriate amine ($HNR^1R^2$), such as ammonia or methylamine. The reaction is easily monitored by TLC and the reaction time is in general from a few minutes to several hours.

Also, an addition salt of the hydroxylamine (II) may be reacted with an alkali metal cyanate, such as potassium cyanate, in, for example, water to give a compound of formula (I) wherein $R^1$ and $R^2$ are hydrogen.

The aforementioned hydroxylamine (II) may be readily prepared by standard synthetic procedures from corresponding carbonyl compound, i.e. ketone or aldehyde, alcohol compound or halogen compound. For example, suitable carbonyl compound is converted to its oxime and then reduced to the requisite hydroxylamine (II) with a suitable reducing agent (for example, see R. F. Borch et al, J. Amer. Chem. Soc., 1971, 93, p 2897). Reducing agents of choice are, but not limited to, sodium cyanoborohydride and borane complexes such as borane-pyridine, borane-triethylamine and borane-dimethylsulfide. However, trimethylsilane in trifluoroacetic acid (TFA) may also be employed.

Alternatively, hydroxylamine (II) can be easily prepared by treating the corresponding alcohol (Q—OH) with, for example, N,O-bis(tert-butoxycarbonyl)-hydroxylamine under Mitsunobtu-type reaction conditions followed by acid catalyzed hydrolysis (for example, employing TFA or HCl-MeOH solution) of the N,O-protected intermediate (see JP (KOKAI) 45344/1989). A suitable condensing reagent in the Mitsunobu reaction is di-($C_1$–$C_4$)alkyl azodicarboxylate in the presence of a triarylphosphine, for example, diethyl azodicarboxylate in the presence of triphenylphosphine. Reaction-inert solvents of choice include $CH_2Cl_2$, THF, dimethylformamide or toluene. The reaction temperature is preferably in the range of 0° C. to reflux temperature of the solvent, e.g. 0° to 100° C., but if necessary, temperatures lower or higher can be adopted. The reaction easily monitored by TLC. The reaction time is in general from a few minutes to several hours.

The aforementioned hydroxylamine (II) may also be prepared from suitable halide compound (e.g. Q—Cl) by reaction with O-protected hydroxylamine and subsequent deprotection (see W. P. Jackson et. al., J. Med. Chem., 1989, 31, p 499).

The hydroxylamine of formula (II) thus obtained by the above mentioned representative procedure is isolated by standard methods and purification can be achieved by conventional means, such as recrystallization and chromatography.

In another embodiment, compounds of the formula (I) are prepared as illustrated in Scheme 2. Q is as previously defined and $R^3$ is phenyl, mono-substituted phenyl or $C_1$–$C_4$ alkyl and $R^4$ is phenyl or mono-substituted phenyl.

Scheme 2

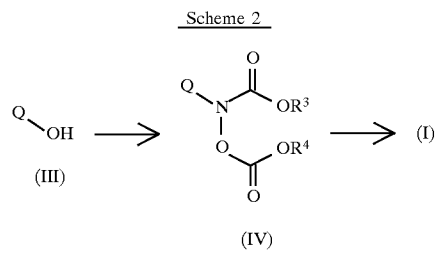

In the reaction sequence in Scheme 2, the compounds (I) are obtained by treating the alcohol (III) under Mitsunobu reaction conditions with a suitable N,O-bis-(carboxy) hydroxylamine,preferably N,O-bis(phenoxycarbonyl) hydroxylamine, and subsequently converting the resulting product (IV) to (I) by treatment with an appropriate amine ($HNR^1R^2$) such as ammonia, methylamine or dimethylamine (A. O. Stewart and D. W. Brooks., J. Org. Chem., 1992, 57, p 5020) in the absence or presence of a reaction-inert solvent. Reaction-inert solvents of choice include water, methanol, ethanol, THF and benzene. The reaction temperature is preferably in the range of −78° C. to reflux temperature of the solvent, but if necessary, temperatures lower or higher can be adopted. The reaction was easily monitored by TLC. The reaction time is in general from a few minutes to several hours. A suitable condensing reagent in the Mitsunobu reaction is di-($C_1$–$C_4$)alkyl azodicarboxylate in the presence of a triarylphosphine, for example, diethyl azodicarboxylate in the presence of triphenylphosphine.

In the case that $(Y)_m$ is C≡C, the hydroxylamine intermediate (II) may be prepared from a suitable aryl halide compound (VI, Z is Br or I) or triflate derivative (VI, Z is $OSO_2CF_3$), and a corresponding N,O-protected alkynyl hydroxylamine (e.g, N,O-bis(tert-butoxycarbonyl)prop-2-yn-1-ylhydroxylamine and the like) by a coupling reaction in the presence of a palladium catalyst (e.g., $Pd(PPh_3)_2Cl_2$, $Pd(PPh_3)_4$, $Pd(PPh_3)_2Cl_2$-CUI, etc.) and subsequent deprotection. Alternatively, the hydroxylamine intermediate (II) may be prepared from a suitable aryl halide compound (i.e. bromoaryl or iodoaryl derivative and the like) or triflate derivative, and a corresponding alkynyl alcohol (e.g., propargyl alcohol and the like) by a coupling reaction in the presence of a palladium catalyst (e.g., $Pd(PPh_3)_2Cl_2$, $Pd(PPh_3)_4$, $Pd(PPh_3)_2Cl_2$-CuI, etc.). Obtained alcohol may be transformed to (II) as described herein before.

In the case that $(Y)_m$ is oxygen or sulfur, the hydroxylamine intermediate (II) may be prepared by an alkylation reaction from a suitable phenol or thiophenol compound (VI, Z is OH or SH) and suitable alkyl halide, or alkyl sulfonyloxy compound (e.g., a 2-(protected hydroxy)ethyl bromide), followed by removal of the protecting group to give (III). Obtained alcohol may be transformed to (II) as described herein before. When the alkyl halide or alkyl sulfonyloxy compound is reacted with the phenol or thiophenol, an alkali or alkaline earth metal carbonate, hydroxide or hydride such as sodium carbonate, potassium carbonate, sodium hydroxide, potassium hydroxide, sodium hydride or potassium hydride is usually used. Suitable solvents that do not react with reactants and/or products are, for example, N,N-dimethylformamide, dimethylsulfoxide, acetone or THF. Reaction temperature is preferably in the range of from ambient temperature to the reflux temperature of the solvent, e.g. 15° to 150° C., but if necessary, temperatures lower or higher can be adopted. The reaction is easily monitored by thin-layer chromatography (TLC) techniques. The reaction time is in general from a few minutes to several hours.

Pharmaceutically acceptable base salts of compounds of formula (I) may be prepared by methods well known to those skilled in the art, for example, by contacting said compound with a stoichiometric amount of an appropriate alkaline or alkaline earth metal (sodium, lithium, potassium, calcium and magnesium) hydroxide or alkoxide in water or an appropriate organic solvent such as ethanol, isopropanol or the like. Some of the compounds of formula (I) may form acid addition salts by contacting said compound with an appropriate non-toxic acid. Examples of suitable acid addition salts are hydrochloride, sulfate or bisulfate, phosphate or acid phosphate, acetate, fumarate, gluconate, lactate, maleate, succinate, tartrate, methanesulfonate, benzenesulfonate, toluenesulfonate and formate salts. Pharmaceutically acceptable salts of the compounds of formula (I) can be isolated by subsequent precipitation or by removal of the solvent by evaporation.

The intermediates (VI) can be utilized in the preparation of compounds of formula (I), wherein $Ar^1$, $Ar^2$, X and n are as previously defined and Z is halo, (preferably bromo or iodo), OH, SH,. $SR^5$, $OR^5$ or $CH_2OR^5$, wherein $R^5$ is a suitable protecting group, preferably benzyl, 4-methoxyphenyl or tert-butyldimethylsilyl group.

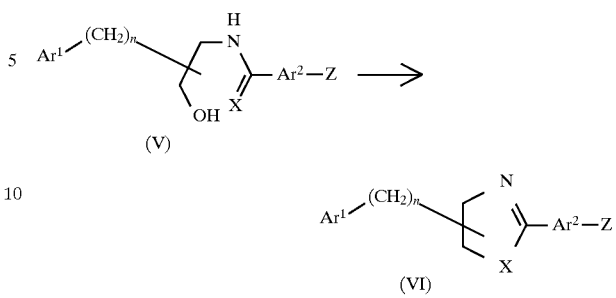

Scheme 3

The said intermediate (VI), wherein Z is halo, $SR^5$, $OR^5$ or $CH_2OR^5$, may be prepared by the reaction of a compound of the formula (V) with a dehydrating agent such as a di-$(C_1-C_4)$alkyl azo-dicarboxylate in the presence of a triarylphosphine, for example, diethyl azodicarboxylate in the presence of triphenylphosphine or alternatively thionyl chloride. Suitable solvents that do not react with reactants and/or products are, for example, THF, $CH_2Cl_2$ or benzene. Reaction temperature is preferably in the range of from 0° C. to the reflux temperature of the solvent, e.g. 0° C. to 80 ° C., but if necessary, temperatures lower or higher can be adopted. The reaction is easily monitored by thin-layer chromatography (TLC) techniques. The reaction time is in general from a few minutes to several hours.

Deprotection of the suitable protecting group $R^5$ will vary with the choice of protecting group. Thus, for example, an arylmethyl group such as benzyl group may be removed, for example, by hydrogenolysis over a catalyst such as palladium-on-charcoal. Alternatively, a protecting group such as 4-methoxyphenyl may be removed oxidatively with, for example, ceric ammonium nitrate. A trialkylsilyl or an aryldi-alkylsilyl group such as tert-butyldimethylsilyl or dimethylphenylsilyl group may be removed, for example, by treatment with a suitable acid such as hydrochloric, sulfuric or TFA, or with an alkali metal or ammonium fluoride such as, for example, sodium fluoride or, preferably, tetrabutylammonium fluoride.

The compounds of the formula (I) and the various intermediate thereto are isolated by standard methods, and purification can be achieved by conventional means, such as recrystallization and chromatography.

The compounds of formula (I) contain one or more asymmetric centers and therefore they are capable of existing in various stereoisomeric forms. The present invention includes all such possible stereomers, both in their pure state and as mixtures thereof.

The compounds of the present invention inhibit the activity of the 5-lipoxy-genase enzyme. This inhibition can be demonstrated in vitro by assays using heparinized Human Whole Blood (HWB), according to the method described in Br. J. Pharmacol.: 99, pp 113–118 (1990), which determines the effect of said compounds on the metabolism of arachidonic acid. In these tests, some preferred compounds show $IC_{50}$ values of 0.1 to 5 μM in HWB assay, with respect to lipoxygenase activity.

The in vivo potency after oral administration of compounds of the invention to ICR mice (male) can be determined using PAF lethality assay in a similar manner as described by J. M. Young et al. (J. M. Young, P. J. Maloney, S. N. Jubb, and J. S. Clark, Prostaglandins, 30, p 545(1985); M. Criscuoli and A. Subissi, Br. J. Pharmac., 90, p 203 (1987); H. Tsunoda, S. Abe, Y. Sakuma, S. Katayama, and K. Katayama, Prostaglandins Leukotrienes and Essential

*Fatty Acids*, 39, p 291 (1990)). In this test, some preferred compounds indicate $ED_{50}$ values in the range of 1 to 10 mg/kg.

The ability of the compounds of the present invention to inhibit the 5-lipoxy-genase enzyme makes them useful for controlling the symptoms induced by the endo-genous metabolites arising from arachidonic acid in a mammalian subject. The compounds are therefore valuable in the prevention and treatment of disease states in which the accumulation of arachidonic acid metabolites are the causative factor; e.g. allergic bronchial asthma, skin disorders, rheumatoid arthritis and osteoarthritis. Thus, the compounds of the present invention and their pharmaceutically acceptable salts are of particular use in the treatment or prevention of inflammatory diseases in a human subject.

For treatment or prevention of the various conditions described above, the compounds of the formula (I) of this invention can be administered to a human subject either alone, or preferably in combination with pharmaceutically acceptable carriers or diluents in a pharmaceutical composition according to standard pharmaceutical practice.

The compounds can be administered to human subjects by various conventional routes of administration including oral and parenteral. When the compounds are administered orally to humans for the treatment or prevention of an inflammatory disease, the dose range will be from about 0.1 to 20 mg/kg of body weight of the subject to be treated per day, preferably from about 0.5 to 15 mg/kg of body weight per day, in single or divided doses. If parenteral administration is desired, then an effective dose will be from about 0.05 to 5 mg/kg of body weight of the human subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s—singlet, d—doublet, t—triplet, m—multiplet and br—broad.

Example 1

(+)-N-[3-[3-(4,5-Dihydro-4(R)-phenyloxazol-2-yl)phenyl]-2-propyn-1-y]-N-hydroxyurea A. (+)-2-(3-Iodobenzamido)-2(R)-phenylethan-1-ol To a vigorously stirred solution of 3-iodobenzoyl chloride (16.79 g, 63 mmol) in dichloromethane (300 ml) was rapidly added a solution of (R)-(–)-2-phenylglycinol (8.64 g, 63 mmol) in dichloromethane (50 ml). The reaction mixture was stirred for 3 hours and crude product collected by filtration. Recrystallization from isopropyl alcohol gave (+)-2-(3-iodobenzamido)-2(R)-phenylethan-1-ol as white needles (14.74 g, 64%).

mp: 154°–156° C.; IR (KBr) √: 3400, 3300, 1635, 1538, 700 cm$^{-1}$. $^1$H NMR (CDCl$_3$) δ: 8.14 (t, J=1.5 Hz, 1H), 7.85 (d, J=7 Hz, 1H), 7.77 (d, J=7 Hz, 1H), 7.4–7.3 (m, 5H), 7.19 (t, J=7 Hz, 1H), 6.78 (br. s, 1H), 5.3–5.2(m, 1H), 4.02 (d, J=5 Hz, 2H), 2.35 (br. s, 1H). $[\alpha]_D$:=+52.3° (c=0.44, DMF)

B. (+)-4,5-Dihydro-2-(3-iodophenyl)-4(R)-phenyloxazole

To a mixture of (+)-2-(3-iodobenzamido)-2(R)-phenylethan-1-ol (14.70 g, 40 mmol) and triphenylphosphine (13.64 g, 52 mmol) in dry tetrahydrofuran (350 ml) was added dropwise a solution of diethyl azodicarboxylate (10.52 g, 52 mmol) in dry tetrahydrofuran (15 ml). The reaction mixture was stirred for 18 h and volatiles removed by evaporation. The residue was purified by column chromatography on silica gel eluting with ethyl acetate-hexane (1:8) to afford (+)-4,5-dihydro-2-(3-iodophenyl)-4(R)-phenyloxazole (7.81 g, 56%) as a liquid.

IR (film)√: 3080, 3020, 2960, 2900, 1645, 1560, 1355, 955, 820, 800 cm$^{-1}$. $^1$H NMR (CDCl$_3$) δ: 8.41 (t, J=1.5 Hz, 1H), 7.98 (dd, J=8, 1.5 Hz, 1H), 7.83 (dd, J=8, 1.5 Hz, 1H), 7.42–7.24 (m, 5H), 7.18 (t, J=8 Hz, 1H), 5.39 (dd, J=10, 8.5 Hz, 1H), 4.80 (dd, J=10, 8.5 Hz, 1H), 4.29 (t, J=8.5 Hz, 1H). $[\alpha]_D$:=+11.42° (c=0.42, CH$_2$Cl$_2$)

C. N,O-Di(tert-butoxycarbonyl)-[3-[3-(4,5-dihydro-4(R)-phenyloxazol-2-yl)-phenyl]-2-propyn-1-yl]hydroxylamine A mixture of (+)-4,5-dihydro-2-(3-iodophenyl)-4(R)-phenyloxazole (7.76 g, 22.2 mmol), [N,O-di(tert-butoxycarbonyl)-2-propyn-1-yl]hydroxylamine (9.03 g, 33.3 mmol) and bis(triphenylphosphine)palladium (II) chloride (780 mg, 1.1 mmol) in triethylamine (30 ml), was stirred for 1 hour under a nitrogen atmosphere, CuI (420 mg, 2.2 mmol) added and the reaction mixture stirred for a further 16 hours. Insoluble material was removed by filtration and the filtrate concentrated under reduced pressure. The resulting residue was purified by column chromatography on silica gel eluting with ethyl acetate-hexane=1:7 to afford of N,O-di(tert-butoxy-carbonyl)-[3-[3-(4,5-dihydro-4 (R)-phenyloxazol-2-yl)phenyl]-2-propyn- 1-yl]-hydroxylamine (7.6 g, 70 %) as brittle off-white flakes.

$^1$H NMR (CDCl$_3$) δ: 8.11 (t, J=1.5 Hz, 1H), 7.99 (dd, J=8, 1.5 Hz, 1H), 7.55 (dd, J=8, 1.5 Hz, 1H), 7.40–7.28 (m, 6H), 5.39 (dd, J=10, 7 Hz, 1H), 4.80 (dd, J=10, 7 Hz, 1H), 4.56 (br.s, 2H), 4.28 (t, J=10 Hz, 1H), 1.53 (s, 9H), 1.51 (s, 9H).

D. (+)-N-[3-[3-(4,5-Dihydro-4(R)-phenyloxazol-2-yl) phenyl]-2-propyn-1-yl]-N-hydroxyurea To a solution of N,O-di(tert-butoxycarbonyl)-[3-[3-(4,5-dihydro-4(R)-phenyl-oxazol-2-yl)phenyl]-2-propyn-1-yl] hydroxylamine (1.99 g, 4 mmol) in dichloromethane (30 ml) cooled to 0° C. was slowly added trifluoroacetic acid (10 ml). The reaction mixture was allowed to warm to room temperature, stirred an additional 30 min., and then poured into a saturated aqueous NaHCO$_3$ solution (100 ml). The mixture was extracted with dichloromethane (3×30 ml) and the organic phase washed with brine (20 ml), dried (MgSO$_4$) and evaporated. The resulting residue was dissolved in tetrahydrofuran (20 ml) and trimethylsilyl isocyanate (0.84 ml, 6.3 mmol) added. After stirring for 10 min. precipitation of product occurred. Methanol (1 ml) was added and solvent was removed by evaporation. The resulting solids were recrystallized from ethyl acetate to afford the title compound (0.98 g, 72 %) as white solids.

mp: 182°–183.5° C. (decomp.) IR (KBr) ν: 3800, 3500, 1640, 1440, 1100, 995, 950, 700 cm$^{-1}$. $^1$H NMR (DMSO-d$_6$) δ: 9.65 (s, 1H), 7.94 (s, 1H), 7.92 (d, J=8 Hz, 1H), 7.62 (d, J=8 Hz, 1H), 7.53 (t, J=8 Hz, 1H), 7.46–7.28 (m, 5H), 6.58 (s, 2H), 5.42(dd, J=8.5, 10 Hz, 1H), 4.86 (dd, J=8.5, 10 Hz, 1H), 4.33 (s, 2H), 4.21 (t, J=8.5 Hz, 1H). [α]$_D$:=+1.7° (c=0.18, DMF)

Elemental analysis:
Calc: C: 67.33%; H: 5.14%; N: 12.4%
Found: C; 67.57%; H: 5.17%; N: 12.17%

Example 2
(+)-N-[3-[3-(4,5-Dihydro-4(R)-phenyloxazol-2-yl)phenyl]-2-propyn-1-yl]-N-hydroxy-N'-methylurea The title compound was prepared in a similar manner to example 1 employing methyl isocyanate instead of trimethylsilyl isocyanate as white solids (recrystallized from ethyl acetate/methanol).

mp: 173.1°–174.8° C.; IR (KBr) ν: 3360, 3100, 2850, 1670, 1640, 1540, 1410, 1340, 1100, 990, 950 cm$^{-1}$. $^1$H NMR (DMSO-d$_6$) δ: 9.59(s, 1H), 7.92(d, J=7.7 Hz, 2H), 7.61(d, J=7.7 Hz, 1H), 7.52(t, J=7.3 Hz, 1H), 7.39–7.31(m, 1H), 7.29–7.28(m, 5H), 5.42(dd, J=8, 10 Hz, 1H), 4.90–4.82 (m, 1H), 4.34(s, 2H), 4.25–4.18(m, 1H), 2.61(d, J=4.8 Hz, 3H). [α]$_D$:=+11.0° (c=0.2, methanol)

Example 3
(+)-N-[3-[3-(4,5-Dihydro-4(R)-phenyloxazol-2-yl)phenyl]-2-propyn-1-yl]-N'-ethyl-N-hydroxyurea The title compound was prepared in a similar manner to example 1 employing ethyl isocyanate instead of trimethylsilyl isocyanate as white solids (recrystallized from ethyl acetate/hexane).

mp: 141.2°–143.0° C. IR (KBr) ν: 3330, 3150–2850, 1670, 1660, 1530, 1440, 1340, 1240, 1100, 990, 950, cm$^{-1}$. $^1$H NMR (DMSO-d$_6$) δ: 9.59 (s, 1H), 7.92 (d, J=9 Hz, 2H), 7.62–7.17(m, 8H), 5.42 (t, J=8 Hz, 1H), 4.86 (t, J=8.8 Hz, 1H), 4.33 (s, 2H), 4.21 (t, J=8 Hz, 1H), 3.13–3.03 (m, 2H), 1.01 (t, 7.3 Hz, 3H). [α]$_D$:=+8.0° (c=0.2, methanol)

Example 4
(+)-N-[3-[3-(4,5-Dihydro-4(R)-phenyloxazol-2-yl)phenyl]-2-propyn-1-yl]-N-hydroxy-N'-isopropylurea The title compound was prepared in a similar manner to example 1 employing isopropyl isocyanate instead of trimethylsilyl isocyanate as white solids (recrystallized from ethyl acetate/hexane).

mp: 111.8°–112.9° C. (decomp.); IR (KBr) ν: 3420, 3250, 2970, 1670, 1640, 1510, 1350, 1230, 1100, 1000, 950 cm$^{-1}$. $^1$H NMR (DMSO-d$_6$) δ: 9.61(s, 1H), 7.94–7.90(m, 3H), 7.61–7.52(m, 1H), 7.49–7.28(m, 5H), 6.85(d, J=8.4 Hz, 1H), 5.42(dd, J=8.4, 9.9 Hz, 1H), 4.86(dd, J=8.4, 9.90 Hz, 1H), 4.33(s, 2H), 4.20(t, J=8.4 Hz, 1H), 3.81–3.73(m, 1H), 1.08 (d, J=6.6 Hz, 6H). [α]$^D$:=+12.0° (c=0.2, methanol)

Example 5
(−)-N-[3-[3-(4,5-Dihydro-4(S)-phenyloxazol-2-yl)phenyl]-2-propyn-1-yl]-N-hydroxyurea, The title compound was prepared in a similar manner to example 1 employing (S)-(+)-2-phenylglycinol instead of (R)-(−)-2-phenylglycinol as white solids (recrystallized from ethanol).

mp: 186.7°–188.0° C. (decomp.); IR (KBr) ν: 3800, 3500, 1640, 1440, 1100, 995, 950, 700 cm$^{-1}$. $^1$H NMR (DMSO-d$_6$) δ: 9.65 (s, 1H), 7.94 (s, 1H), 7.92 (d, J=8 Hz, 1H), 7.62 (d, J=8 Hz, 1H), 7.53 (t, J=8 Hz, 1H), 7.46–7.28 (m, 5H), 6.58 (s, 2H), 5.42(dd, J=8.5, 10 Hz, 1H), 4.86 (dd, J=8.5, 10 Hz, 1H), 4.33 (s, 2H), 4.21 (t, J=8.5 Hz, 1H).

Example 6
(−)-N-[3-[3-(4,5-Dihydro-4(S)-phenyloxazol-2-yl)phenyl]-2-propyn-1-yl]-N-hydroxy-N'-methylurea The title compound was prepared in a similar manner to example 5 employing methyl isocyanate instead of trimethylsilyl isocyanate as white needles (recrystallized from ethyl acetate).

mp: 163°–165° C.; IR (KBr) ν: 3400, 1670, 1640, 700 cm$^{-1}$. $^1$H NMR (DMSO-d$_6$) δ: 9.56 (s, 1H), 7.94 (s, 1H), 7.93 (d, J=8 Hz, 1H), 7.58 (t, J=8 Hz, 1H), 7.52 (t, J=8 Hz, 1H), 7.44–7.28 (m, 5H), 7.14 (q, J=5 Hz, 1H), 5.41 (dd, J=8.5, 10 Hz, 1H), 4.89 (dd, J=8.5, 10 Hz, 1H), 4.34 (s, 2H), 4.21 (t, J=8.5 Hz, 1H), 2.61 (d, J=5 Hz, 3H).

Example 7
(+)-N-[3-[3-[4,5-Dihydro-4(R)-(4-fluorophenyl)oxazol-2-yl]phenyl]-2-propyn-1-yl]-N-hydroxyurea The title compound was prepared in a similar manner to example 1 employing (R)-(−)-2-(4-fluorophenyl)glycinol instead of (R)-(−)-2-phenylglycinol as white solids (recrystallized from ethyl acetate/methanol).

mp: 180.9°–181.4° C.; IR (KBr) ν: 3420, 3200–3300, 2850, 1640, 1510, 1440, 1240, 1100, 990, 950 cm$^{-1}$. $^1$H NMR (DMSO-d$_6$) δ: 9.64(s, 1H), 7.94–7.91(m, 2H), 7.63–7.61(m, 1H), 7.52(t, J=7.7 Hz, 1H), 7.35(dd, J=5.5, 8.8 Hz, 2H), 7.19(t, J=8.8 Hz, 2H), 6.58(s, 2H), 5.44(t, J=8.4 Hz, 1H), 4.86(t, J=8.4 Hz, 1H), 4.34(s, 2H), 4.19(t, J=8.4 Hz, 1H). [α]$_D$:=+6.5° (c=0.2, methanol)

Example 8
(−)-N-[3-[3-(4,5-Dihydro-4(R)-phenylthiazol-2-yl)phenyl]-2-propyn-1-yl]-N-hydroxyurea A. N-(1-tert-Butyldimethylsilyloxy-2(R)-phenylethan-2-yl)-3-iodobenzamide To a mixture of (+)-2-(3-iodobenzamido)-2(R)-phenylethan-1-ol (10 g, 27.2 mmol, prepared as in example 1) and imidazole (4.6 g, 68 mmol) in N,N-dimethylformamide (50 ml) was added tert-butyldimethylchlorosilane (6.2 g, 41 mmol) in one-portion. The reaction mixture was stirred at ambient temperature for 2 h and then partitioned between ethyl acetate (100 ml) and water (100 ml). The aqueous layer was separated and extracted with ethyl acetate (3×50 ml). The combined organic phase was washed with 1N HCl (100 ml), aqueous saturated NaHCO$_3$ solution (100 ml) and brine (100 ml), dried (MgSO$_4$), and concentrated under reduced pressure. The resulting residue was purified by column chromatography on silica gel eluting with ethyl acetate/hexane (=1:8) to afford N-(1-tert-butyldimethyl-silyloxy-2(R)-phenylethan-2-yl)-3-iodobenzamide (13.1 g, quant.) as a pale yellow liquid.

$^1$H NMR (CDCl$_3$) δ: 8.19 (s, 1H), 7.88 (d, J=8 Hz, 1H), 7.80 (d, J=8 Hz, 1H), 7.39–7.20 (m, 6H), 6.99 (br. s, 1H), 5.24–5.21(m, 1H), 4.06 (dd, J=4.4, 10 Hz, 1H), 3.94 (dd, J=4.0, 10 Hz, 1H), 0.92 (s, 9H), 0.04 (s, 6H).

B. N-(1-tert-Butyldimethylsilyloxy-2(R)-phenylethan-2-yl)-3-iodobenzthiamide

To a solution of N-(1-tert-butyldimethylsilyloxy-2(R)-phenylethan-2-yl)-3-iodobenzamide (13.1 g, 27.2 mmol) in 1,2-dimethoxyethane (80 ml) was added Lawesson's reagent (8.2 g, 20 mmol). The reaction mixture was stirred at ambient temperature for 1 h and then at 60° C. for 2 hours, cooled and poured into water (100 ml). The mixture was extracted with CH$_2$Cl$_2$ (2×50 ml), washed with brine (100 ml), dried (MgSO$_4$) and concentrated under reduced pressure. The resulting residue was purified by column chromatography on silica gel eluting with ethyl acetate/hexane (=1:7) to afford N-(1-tert-butyldimethylsilyloxy-2(R)-phenyl-ethan-2-yl)-3-iodobenzthiamide (4.99 g, 50%) as a yellow liquid.

$^1$H NMR (CDCl$_3$) δ: 8.30 (d, J=1.8 Hz, 1H), 7.87–7.79 (m, 2H), 7.39–7.32 (m, 5H), 7.17 (t, J=7.7 Hz, 1H), 5.71 (t, J=9.1 Hz, 1H), 3.87–3.79 (m, 2H), 3.35 (dd, J=9.5, 11 Hz, 1H), 0.9 (s, 6H), 0.3 (s, 9H).

C. 4,5-Dihydro-2-(3-iodophenyl)-4(R)-phenylthiazole

To a solution of N-(1-tert-butyldimethylsilyloxy-2(R)-phenylethan-2-yl)-3-iodobenzthiamide (8.1 g, 16 mmol) in THF (70 ml) was added dropwise tetrabutyl-ammonium fluoride (1M in THF, 21 ml). The reaction mixture was stirred at room temperature for 4 hours, solvent removed by evaporation and the resulting residue was purified by column chromatography on silica gel eluting with ethyl acetate/n-hexane (=1:7) to afford 4,5-dihydro-2-(3-iodophenyl)-4(R)-phenylthiazole (2.46 g, 41%).

$^1$H NMR (CDCl$_3$) δ: 8.30 (s, 1H), 7.88–7.80 (m, 2H), 7.39–7.31 (m, 5H), 7.17 (t, J=8 Hz, 1H), 5.70 (t, J=9 Hz, 1H), 3.83 (dd, J=9, 11 Hz, 1H), 3.34 (dd, J=9.5, 11 Hz, 1H).

Further elution with ethyl acetate/n-hexane (=1:1) gave 2-amino-N-(3-iodobenzthiazoyl)-2(R)-phenylethan-1-ol (0.75 g, 12%).

$^1$H NMR (CDCl$_3$) δ: 8.28 (br. s, 1H), 8.12 (t, J=1.8 Hz, 1H), 7.82–7.72 (m, 2H), 7.44–7.30 (m, 1H), 7.14 (t, J=8 Hz, 1H), 5.86–5.80 (m, 1H), 4.17–4.07 (m, 3H).

D. (−)-N-[3-[3-(4,5-Dihydro-4(R)-phenylthiazol-2-yl)phenyl]-2-propyn-1-yl]-N-hydroxyurea The title compound was prepared in a similar manner to example 1 from 4,5-dihydro-2-(3-iodophenyl)-4(R)-phenylthiazole as pale yellow solids (recrystallized from ethyl acetate/hexane).

mp: 154.6°–156.8° C.; IR (KBr) √: 3400, 3300, 1640, 1440, 1090, 940 cm$^{-1}$. $^1$H NMR (DMSO-d$_6$) δ: 9.65 (s, 1H), 7.84 (d, J=7.7 Hz, 2H), 7.62–7.46 (m, 2H), 7.39–7.33 (m, 5H), 6.59 (s, 2H), 5.78 (t, J=8.8 Hz, 1H), 4.35 (s, 2H), 3.99 (t, J=9.2 Hz, 1H), 3.34–3.32 (m, 1H). [α]$_D$: =−79° (c=0.2, methanol).

Elemental analysis:

Calc: C: 64.94%; H: 4.88%; N: 11.96%

Found: C: 65.04%; H: 4.74%; N: 11.98%

Example 9

N'-Allyl-N-[3-[3-(4,5-dihydro-4(R)-phenylthiazol-2-yl)phenyl]-2-propyn-1-yl]-N-hydroxyurea The title compound was prepared in a similar manner to example 8 employing allyl isocyanate instead of trimethylsilyl isocyanate.

mp: amorphous IR (KBr) √: 3450, 3200, 1660, 1540, 1420, 910 cm$^{-1}$. $^1$H NMR (DMSO-d$_6$) δ: 9.66 (s, 1H), 7.85–7.82 (m, 2H), 7.61–7.30 (m, 8H), 5.85–5.74 (m, 2H), 5.14–4.98 (m, 2H), 4.35 (s, 2H), 3.99 (dd, J=9, 11 Hz, 1H), 3.68 (t, J=5 Hz, 2H), 3.33–3.27 (m, 1H).

Example 10

(−)-N-[3-[3-(4,5-Dihydro-4(R)-phenyloxazol-2-yl)-2-fluorophenyl]-2-propyn-1-yl]-N-hydroxyurea A. 4,5-Dihydro-2-(2-fluoro-3-iodophenyl)-4(R)-phenyloxazole 4,5-Dihydro-2-(2-fluoro-3-iodophenyl)-4(R)-phenyloxazole was prepared from 2-fluoro-3-iodobenzoyl chloride in a similar manner to that of (+)-4,5-dihydro-2-(3-iodophenyl)-4(R)-phenyloxazole as described in Example 1.

$^1$H NMR (CDCl$_3$) δ: 7.96–7.85 (m, 2H), 7.39–7.28 (m, 5H), 6.97 (t, J=8 Hz, 1H), 5.43 (t, J=10 Hz, 1H), 4.80 (dd, J=8, 10 Hz, 1H), 4.29 (t, J=8 Hz, 1H).

B. 3-[3-[4,5-Dihydro-4(R)-phenyloxazol-2-yl]-2-fluorophenyl]-2-propyn-1-ol

A mixture of 4,5-dihydro-2-(2-fluoro-3-iodophenyl)-4(R)-phenyloxazole (2.28 g, 6.2 mmol), propargyl alcohol (0.22 g, 12.4 mmol) and bis(triphenylphosphine)-palladium(II) chloride (220 mg, 1.1 mmol) in triethylamine (50 ml), was stirred for 1 h under a nitrogen atmosphere, CuI (420 mg, 2.2 mmol) added and the reaction mixture stirred for a further 16 hours. Insoluble material was removed by filtration and the filtrate concentrated under reduced pressure. The resulting residue was purified by column chromatography on silica gel eluting with ethyl acetate-hexane (=1:14) to afford of 3-[3-(4,5-dihydro-4(R)-phenyloxazol-2-yl)-2-fluorophenyl]-2-propyn-1-ol (1.41 g, 77%) as off-white solids.

1H NMR (CDCl$_3$) δ: 7.92 (t, J=7 Hz, 1H), 7.55 (t, J=7 Hz, 1H), 7.36–7.25 (m, 5H), 7.16 (t, J=7 Hz, 1H), 5.43 (t, J=10 Hz, 1H), 4.81 (t, J=8 Hz, 1H), 4.50 (d, J=6 Hz, 2H), 4.32 (dd, J=8, 10 Hz, 1H), 2.05 (t, J=6 Hz, 1H).

C. N,O-Di(tert-butoxycarbonyl)-[3-[3-(4,5-dihydro-4(R)-phenyloxazol-2-yl)-2-fluorophenyl]-2-propyn-1-yl]hydroxylamine To a mixture of 3-[3-(4,5-dihydro-4(R)-phenyloxazol-2-yl)-2-fluorophenyl]-2-propyn-1-ol (1.41 g, 4.8 mmol), N,O-bis(tert-butoxycarbonyl)hydroxylamine (1.11 g, 4.8 mmol) and triphenylphosphine (1.63 g, 6.2 mmol) in dry tetrahydrofuran (350 ml) was added dropwise a solution of diethyl azodicarboxylate (1.08 g, 6.2 mmol) in dry tetrahydrofuran (15 ml). The reaction mixture was stirred for 2 hours and volatiles removed by evaporation. The residue was purified by column chromatography on silica gel eluting with ethyl acetate-hexane (=1:10) to afford N,O-di(tert-butoxycarbonyl)-[3-[3-(4,5-dihydro-4(R)-phenyloxazol-2-yl)-2-fluoro-phenyl]-2-propyn-1-yl]hydroxylamine (1.64 g, 67%) as pale yellow plates.

$^1$H NMR (CDCl$_3$) δ: 7.89 (dt, J=2, 6 Hz, 1H), 7.55 (dt, J=2, 6 Hz, 1H), 7.40–7.28 (m, 5H), 7.14 (t, J=7 Hz, 1H), 5.42 (dd, J=8, 10 Hz, 1H), 4.80 (dd, J=8, 10 Hz, 1H), 4.59 (br. s, 2H), 4.28 (t, J=8 Hz, 1H), 1.53 (s, 9H), 1.51 (s, 9H).

D. (−)-N-[3-[3-(4,5-Dihydro-4(R)-phenyloxazol-2-yl)-2-fluorophenyl]-2-propyn-1-yl]-N-hydroxyurea N,O-Di(tert-butoxycarbonyl)-[3-[3-(4,5-dihydro-4(R)-phenyloxazol-2-yl)-2-fluorophenyl]-2-propyn-1-yl]hydroxylamine was elaborated to the title compound in a similar manner as described in Example 1 as pale yellow solids (recrystallized from ethyl acetate).

mp: 165.5°–167.2° C.; IR (KBr) √: 3400, 3250, 1640, 1000, 740, 700 cm$^{-1}$. $^1$H NMR (DMSO-d$_6$) δ: 9.64 (s, 1H), 7.91 (dt, J=7, 2 Hz, 1H), 7.67 (dt, J=7, 2 Hz, 1H), 7.41–7.30 (m, 6H), 6.58 (s, 2H), 5.44 (dd, J=10, 8 Hz, 1H), 4.84 (dd, J=10, 8 Hz, 1H), 4.38 (s, 2H), 4.19 (t, J=8 Hz, 1H). [α]$_D$:−18° (c=0.2, methanol).

Elemental analysis:

Calc: C: 64.58%; H: 4.56%; N: 11.89%

Found: C: 64.37%; H: 4.47%; N: 11.49%

Example 11

N-[3-[3-(4,5-Dihydro-4(R)-phenyloxazol-2-yl)-4-fluorophenyl]-2-propyn-1-yl]-N-hydroxyurea The title compound was prepared in a similar manner to that of Example 10 employing 2-fluoro-5-iodobenzoyl chloride instead of 2-fluoro-3-iodobenzoyl chloride as white solids (recrystallized from ethyl acetate).

mp: 172.6°–173.8° C.; IR (KBr) ѵ: 3400, 3200 (br.), 1640 cm$^{-1}$. $^1$H NMR (DMSO-d$_6$) δ: 9.63 (s, 1H), 7.95 (dd, J=7, 2 Hz, 1H), 7.69–7.63 (m, 1H), 7.44–7.30 (m, 6H), 6.56 (s, 2H), 5.43 (dd, J=10, 8 Hz, 1H), 4.84 (dd, J=10, 8 Hz, 1H), 4.33 (s, 2H), 4.20 (t, J=8 Hz, 1H).

Example 12

N-[3-[3-(4,5-Dihydro-4(R)-phenyloxazol-2-yl)-4-fluorophenyl]-2-propyn-1-yl]-N-hydroxy-N'-methylurea The title compound was prepared in a similar manner to example 10 employing methyl isocyanate instead of trimethylsilyl isocyanate as white solids (recrystallized from ethyl acetate).

mp: 164.5°–166° C. (decomp.); IR (KBr) ѵ: 3360, 3100, 2850, 1670, 1635, 1495 cm$^{-1}$. $^1$H NMR (DMSO-d$_6$) δ: 9.57 (s, 1H), 7.93 (dd, J=8, 2 Hz, 1H), 7.66–7.62 (m, 1H), 7.43–7.25 (m, 6H), 7.10 (q, J=5 Hz, 1H), 5.43 (dd, J=8, 10 Hz, 1H), 4.8 (dd, J=8, 10 Hz, 1H), 4.32 (s, 2H), 4.19 (t, J=8 Hz, 1H), 2.61 (d, J=5 Hz, 3H).

Example 13

N-[3-[5-(4,5-Dihydro-4(R)phenyloxazol-2-yl)-2-methoxyphenyl]-2-propyn-1-yl]-N-hydroxyurea The title compound was prepared in a similar manner to that of Example 10 employing 3-iodo-4-methoxybenzoyl chloride instead of 2-fluoro-3-iodobenzoyl chloride as white solids (recrystallized from ethyl acetate).

mp: 189.5°–192.0° C. IR (KBr) ѵ: 3470, 2850, 1660, 1640, 1610, 1550, 1280, 1150, 1090, 950 cm$^{-1}$. $^1$H NMR (DMSO-d$_6$) δ: 9.54(s, 1H), 7.92–7.88(m, 2H), 7.39–7.28(m, 5H), 7.17(d, J=9 Hz, 1H), 7.10(d, J=4.4 Hz, 1H), 5.37(dd, J=8, 9.5 Hz, 1H), 4.82(dd, J=8.4, 9.9 Hz, 1H), 4.34(s, 2H), 4.17(t, J=8.4 Hz, 1H), 3.88(s, 3H), 2.61(d, J=5 Hz, 3H).

Example 14

N-[3-[5-(4,5-Dihydro-4(R-phenyloxazol-2-yl)-2-methoxyphenyl]-2-propyn-1-yl]-N-hydroxy-N'-methylurea The title compound was prepared in a similar manner to example 13 employing methyl isocyanate instead of trimethylsilyl isocyanate as white solids (recrystallized from ethyl acetate).

mp: 168.5°–170.0° C.; IR (KBr) ѵ: 3000–3500, 2850, 1650, 1510, 1350, 1280, 1040, 950 cm$^{-1}$. $^1$H NMR (DMSO-d$_6$) δ: 9.59(s, 1H), 7.91–7.88(m, 2H), 7.39–7.28(m, 5H), 7.17(d, J=9 Hz, 1H), 6.55(s, 2H), 5.38(dd, J=8, 9.9 Hz, 1H), 4.78(dd, J=8.4, 9.9 Hz, 1H), 4.34(s, 2H), 4.17(t, J=8.4 Hz, 1H), 3.89(s, 3H).

Example 15

N-[3-[5-(4,5-Dihydro-4(R)-phenyloxazol-2-yl)-2-methylphenyl]-2-propyn-1-yl]-N-hydroxyurea The title compound was prepared in a similar manner to that of Example 10 employing 3-iodo-4-methylbenzoyl chloride instead of 2-fluoro-3-iodobenzoyl chloride as white solids (recrystallized from ethyl acetate).

mp: 169.0°–169.5° C.; IR (KBr) ѵ: 3480, 3350, 3200, 2900,.1640, 1580 cm$^{-1}$. $^1$H NMR (DMSO-d$_6$) δ: 9.61 (s, 1H), 7.90 (s, 1H), 7.81 (dd, J=8, 2 Hz, 1H), 7.43–7.26 (m, 6H), 6.58 (s, 2H), 5.39 (dd, J=10, 8 Hz, 1H), 4.36 (s, 2H), 4.19 (t, J=8 Hz, 1H), 2.43 (s, 3H).

Example 16

N-[3-[5-(4,5-Dihydro-4 (R) -phenyloxazol-2-yl)-2-methylphenyl]-2-propyn-1-yl]-N-hydroxy-N'-methylurea The title compound was prepared in a similar manner to example 15 employing methyl isocyanate instead of trimethylsilyl isocyanate as white solids (recrystallized from ethyl acetate).

mp: 175.8°–176.4° C. (decomp.) IR (KBr) ѵ: 3350, 3100, 2800, 1675, 1640, 1515, 1370 cm$^{-1}$. $^1$H NMR (DMSO-d$_6$) δ: 9.56 (s, 1H), 7.89 (d, J=2 Hz, 1H), 7.81 (dd, J=8, 2 Hz, 1H), 7.43–7.26 (m, 6H), 7.14 (q, J=5 Hz, 1H), 5.40 (dd, J=8, 10 Hz, 1H), 4.84 (dd, J=8, 10 Hz, 1H), 4.36 (s, 2H), 4.19 (t, J=8 Hz, 1H), 2.62 (d, J=5 Hz, 3H), 2.42 (s, 3H).

Example 17

N-[3-[3-(4(S)-Benzyl-4,5-dihydroxazol-2-yl)phenyl]-2-propyn-1-yl]-N-hydroxyurea

The title compound was prepared in a similar manner to example 1 employing (S)-(–)-2-amino-3-phenyl-1-propanol instead of (R)-(–)-2-phenylglycinol as white solids (recrystallized from ethanol).

mp: 167.5°–168.9° C. (decomp.); IR (KBr) ѵ: 3400, 3250, 2850, 1630, 1440, 1350, 1100, 1000, 960, 800 cm$^{-1}$. $^1$H NMR (DMSO-d$_6$) δ: 9.64 (s, 1H), 7.83 (d, J=7.7 Hz, 2H), 7.58 (d, J=7.7 Hz, 1H), 7.48 (t, J=7.3 Hz, 1H), 7.30 (d, J=4.4 Hz, 4H), 7.24–7.21 (m, 1H), 6.59 (s, 2H), 4.59–4.53 (m, 1H), 4.43 (t, J=8 Hz, 1H), 4.34 (s, 2H), 4.11 (t, J=7.7 Hz, 1H), 2.99 (dd, J=6, 13.5 Hz, 1H), 2.79 (dd, J=7, 13.5 Hz, 1H).

Example 18

N-[3-[3-(4(S)-Benzyl-4,5-dihydroxazol-2-yl)phenyl]-2-propyn-1-yl]-N-hydroxy-N'-methylurea The title compound was prepared in a similar manner to example 17 employing methyl isocyanate instead of trimethylsilyl isocyanate as white solids (recrystallized from ethyl acetate/methanol).

mp: 169.6°–170.9° C.; IR (KBr) ѵ: 3420, 3250, 1660, 1540, 1360, 1240, 1100, 990, 800 cm$^{-1}$. $^1$H NMR (DMSO-d$_6$) δ: 9.59 (s, 1H), 7.82 (d, J=7 Hz, 2H), 7.57 (d, J=7.7 Hz, 1H), 7.48 (t, J=8 Hz, 1H), 7.29 (d, J=4 Hz, 4H), 7.23–7.20 (m, 1H), 7.13 (d, J=4.8 Hz, 1H), 4.56–4.53 (m, 1H), 4.43 (t, J=8.4 Hz, 1H), 4.34 (s, 2H), 4.11 (t, J=8 Hz, 1H), 3.16 (dd, J=6, 13.5 Hz, 1H), 2.79 (dd, J=7, 13.5 Hz, 1H), 2.62 (d, J=4.7 Hz, 3H).

Example 19

N-[3-[3-(4(R)-Benzyl-4,5-dihydroxazol-2-yl)phenyl]-2-propyn-1-yl]-N-hydroxyurea

The title compound was prepared in a similar manner to example 1 employing (R)-(+)-2-amino-3-phenyl-1-propanol instead of (R)-(–)-2-phenylglycinol as white solids (recrystallized from ethanol).

mp: 164.3°–166.0° C.; IR (KBr) ѵ: 3400, 3250, 2850, 1630, 1440, 1250, 1100, 1000, 960 cm$^{-1}$. $^1$H NMR (DMSO-d$_6$) δ: 9.65(s, 1H), 7.84–7.80(m, 2H), 7.57(d, J=7.7 Hz, 1H), 7.48(t, J=7.3 Hz, 1H), 7.30–7.20(m, 5H), 6.58(s, 2H), 4.59–4.53(m, 1H), 4.43(t, J=8.8 Hz, 1H), 4.33(s, 2H), 4.11(t, J=7.7 Hz, 1H), 2.99(dd, J=6, 13.5 Hz, 1H), 2.79(dd, J=7, 13.5 Hz, 1H).

Example 20

N-[3-[3-(4(R)-Benzyl-4,5-dihydroxazol-2-yl)phenyl]-2-propyn-1-yl]-N-hydroxy-N'-methylurea The title compound was prepared in a similar manner to example 19 employing methyl isocyanate instead of trimethylsilyl isocyanate as white solids.

mp: 160.2°–161.2° C.; IR (KBr) ѵ: 3450, 3200, 2850, 1660, 1530, 1360, 1230, 1100, 990, 960 cm$^{-1}$. $^1$H NMR (DMSO-d$_6$) δ: 9.60(s, 1H), 7.82(d, J=6.6 Hz, 2H), 7.57(d, J=7.7 Hz, 1H), 7.48(t, J=8 Hz, 1H), 7.31–7.12(m, 6H), 4.59–4.51(m, 1H), 4.43(t, J=8 Hz, 1H), 4.34(s, 2H), 4.41(t, J=7.7 Hz, 1H), 2.99(dd, J=6, 13.5 Hz, 1H), 2.80(dd, J=7, 13.5 Hz, 1H), 2.62(d, J=4.8 Hz, 3H).

Example 21
N-[4-[3-(4,5-Dihydro-4(R)-phenyloxazol-2-yl)phenyl-3-butyn-2-yl]-N-hydroxyurea A. 2-(3-Bromobenzamido)-2(R)-phenylethan-1-ol To a vigorously stirred solution of 3-bromobenzoyl chloride (13 g, 58 mmol) in dichloromethane (500 ml) was rapidly added a solution of (R)-(−)-2-phenyl-glycinol (10.5 g, 76 mmol) in dichloromethane (50 ml). The reaction mixture was stirred for 3 h and insolubles removed by filtration. Concentration of the filtrate gave 2-(3-bromobenzamido)-2(R)-phenylethan-1-ol as colorless solids (18.5 g, quant).

$^1$H NMR (CDCl$_3$) δ: 7.95 (t, J=1.8 Hz, 1H), 7.74 (d, J=7.7 Hz, 1H), 7.65 (d, J=8 Hz, 1H), 7.39–7.29 (m, 7H), 6.83 (br s, 1H), 5.28–5.23 (m, 1H), 4.02 (d, J=4.4 Hz, 2H).

B. 2-(3-Bromophenyl)-4,5-dihydro-4(R)-phenyloxazole

To a mixture of 2-(3-bromobenzamido)-2(R)-phenylethan-1-ol (18 g, 56 mmol) and triphenylphosphine (19.2 g, 73 mmol)) in dry tetrahydrofuran (350 ml) cooled to −60° C. was added dropwise diethyl azodicarboxylate (12 ml, 73 mmol). The reaction mixture was allowed to warm to ambient temperature, stirred for 18 h and volatiles removed by evaporation. The residue was purified by column chromatography on silica gel eluting with ethyl acetate-hexane (=1:7) to afford 2-(3-bromophenyl)-4,5-dihydro-4(R)-phenyloxazole (10.9 g, 65%) as a pink liquid.

$^1$H NMR (CDCl$_3$) δ: 8.21 (t, J=1.8 Hz, 1H), 7.98–7.94 (m, 1H), 7.66–7.61 (m, 1H), 7.39–7.28 (m, 6H), 5.39 (dd, J=8, 10 Hz, 1H), 4.81 (dd, J=8, 10 Hz, 1H), 4.29 (t, J=8 Hz, 1H).

C. N-[4-[3-(4,5-Dihydro-4(R)-phenyloxazol-2-yl)phenyl]-3-butyn-2-yl]hydroxylamine A mixture of 2-(3-bromophenyl)-4,5-dihydro-4(R)-phenyloxazole (4.5 g, 15 mmol), [N,O-di(tert-butoxycarbonyl)-3-butyn-2-yl]hydroxylamine (6.4 g, 22 mmol) and bis(triphenylphosphine)palladium (II) chloride (522 mg, 0.75 mmol) in triethyl-amine (15 ml), was stirred at 75° C. for 3 hours under a nitrogen atmosphere. The reaction mixture was cooled and concentrated under reduced pressure. The residue was extracted with ethyl acetate (3×50 ml) and washed with 1N HCl (100 ml), aqueous 4% NaHCO$_3$ solution (100 ml) and brine (100 ml). The organic phase was dried (MgSO$_4$) and concentrated under reduced pressure. The resulting residue was purified by column chromatography on silica gel eluting with ethyl acetate-hexane (=1:7) to afford crude N,O-di(tert-butoxycarbonyl)-[3-[3-(4,5-dihydro-4(R)-phenyloxazol-2-yl)phenyl]-3-butyn-2-yl]hydroxylamine (4.1 g).

To a solution of the protected hydroxylamine obtained as above in dichloro-methane (40 ml) cooled to 0° C. was slowly added trifluoroacetic acid (6.1 ml, 79 mmol). The reaction mixture was allowed to warm to room temperature, stirred an additional 30 min., and then poured into a saturated aqueous NaHCO$_3$ solution (100 ml). The mixture was extracted with dichloromethane (2×50 ml) and the organic phase washed with water (100 ml), brine (120 ml), dried (MgSO$_4$) and evaporated. The resulting residue was purified by column chromatography on silica gel eluting with ethyl acetate-hexane (=1:1) to give N-[4-[3-(4,5-dihydro-4(R)-phenyloxazol-2-yl)phenyl]-3-butyn-2-yl]hydroxylamine (1.4 g, 58%) as orange oil.

$^1$H NMR (CDCl$_3$) δ: 8.14 (s, 1H), 7.97 (d, J=8 Hz, 1H), 7.56 (d, J=8 Hz, 1H), 7.40–7.28 (m, 7H), 5.42–5.35 (m, 1H), 5.25 (br s, 1H), 4.80 (t, J=8.5 Hz, 1H), 4.31–4.25 (m, 1H), 4.13–4.02 (m, 1H), 1.43 (d, J=7 Hz, 3H).

D. N-[4-[3-(4,5-Dihydro-4(R)-phenyloxazol-2-yl)phenyl-3-butyn-2-yl]-N-hydroxyurea To a solution of N-[4-[3-(4,5-dihydro-4(R)-phenyloxazol-2-yl)phenyl]-3-butyn-2-yl]hydroxylamine (1.3 g, 4.2 mmol) in THF (13 ml) was added trimethyl-silyl isocyanate (0.84 ml, 6.3 mmol), and the mixture stirred at room temperature for 2 hours. Methanol (10 ml) was added and 10 min. later solvent was removed by evaporation. The resulting residue was purified by column chromatography on silica gel eluting with ethyl acetate to give the title compound (0.9 g, 64%) as colorless amorphous solids.

mp: amorphous; IR (KBr) δ: 3500, 3400, 2900, 1650, 1560, 1360, 960 cm$^{-1}$. $^1$H NMR (DMSO-d$_6$) δ: 9.36 (s, 1H), 7.91 (d, J=1.4 Hz, 2H), 7.59 (d, J=8 Hz, 1H), 7.51 (t, J=7.3 Hz, 1H), 7.39–9.29 (m, 5H), 6.57 (s, 2H), 5.42 (t, J=10 Hz, 1H), 5.14 (dd, J=6.6, 14 Hz, 1H), 4.86 (t, J=10 Hz, 1H), 4.21(t, J=8 Hz, 1H), 1.37 (d, J=7 Hz, 3H).

Example 22
N-[4-[3-(4,5-Dihydro-4(R)-phenyloxazol-2-yl)phenyl-3-butyn-2-yl]-N-hydroxyurea(Enantiomer One)

N-[4-[3-(4,5-Dihydro-4(R)-phenyloxazol-2-yl)phenyl-3-butyn-2-yl]-N-hydroxyurea (example 21) was separated on a chiral stationary support (CHIRALPAK OJ (Daicel Chemical Industries) 0.46×25 cm; mobile phase: ethanol/hexane (20:80): flow rate 1 ml/min; temperature=room temperature; 1=230 nm) to afford title compound (example 22, retention time=21.4 min.).

$^1$H NMR (DMSO-d$_6$) δ: 9.36 (s, 1H), 7.91 (d, J=1.4 Hz, 2H), 7.59 (d, J=8 Hz, 1H), 7.51 (t, J=7.3 Hz, 1H), 7.39–9.29 (m, 5H), 6.57 (s, 2H), 5.42 (t, J=10 Hz, 1H), 5.14 (dd, J=6.6, 14 Hz, 1H), 4.86 (t, J=10 Hz, 1H), 4.21 (t, J=8 Hz, 1H), 1.37 (d, J=7 Hz, 3H).

Examples 23
N-[4-[3-(4,5-Dihydro-4(R)-phenyloxazol-2-yl)phenyl-3-butyn-2-yl]-N-hydroxyurea(Enantiomer Two)

N-[4-[3-(4,5-Dihydro-4(R)-phenyloxazol-2-yl)phenyl-3-butyn-2-yl]-N-hydroxyurea (example 21) was separated on a chiral stationary support (CHIRALPAK OJ (Daicel Chemical Industries) 0.46×25 cm; mobile phase: ethanol/hexane (20:80): flow rate 1 ml/min; temperature=room temperature; 1=230 nm) to afford title compound (example 23, retention time=36.5 min.).

$^1$H NMR (DMSO-d$_6$) δ: 9.36 (s, 1 H), 7.91 (d, J=1.4 Hz, 2H), 7.59 (d, J=8 Hz, 1H), 7.51 (t, J=7.3 Hz, 1H), 7.39–9.29 (m, 5H), 6.57 (s, 2H), 5.42 (t, J=10 Hz, 1H), 5.14 (dd, J=6.6, 14 Hz, 1H), 4.86 (t, J=10 Hz, 1H), 4.21 (t, J=8 Hz, 1H), 1.37 (d, J=7 Hz, 3H).

Example 24
N-[4-[3-(4,5-Dihydro-5-phenyloxazol-2-yl)phenyl]-3-butyn-2-yl]-N-hydroxyurea The title compound was prepared in a similar manner to example 21 employing 2-amino-1-phenylethlanol instead of (R)-(−)-2-phenylglycinol as white solids (recrystallized from ethyl acetate).

mp: 145.1°–146.4° C.; IR (KBr) √: 3400, 3200, 2900, 1640, 1590, 1420, 1080, 1000, 960 cm$^{-1}$; $^1$H NMR (DMSO-d$_6$) δ: 9.38 (s, 1H), 7.93–7.89 (m, 2H), 7.60–7.35 (m, 7H), 6.56 (s, 2H), 5.79 (t, J=6.7 Hz, 1H), 5.13 (m, 1H), 4.45 (dd, J=10, 15 Hz, 1H), 3.84 (dd, J=7, 15 Hz, 1H), 1.37 (d, J=7 Hz, 3H).

Example 25
N-[4-[3-(4(S)-Benzyl-4,5-dihydroxazol-2-yl)phenyl]-3-butyn-2-yl]-N-hydroxy-N'-methylurea The title compound was prepared in a similar manner to example 21 employing (S)-(−)-2-amino-3-phenyl-1-propanol instead of (R)-(−)-2-phenylglycinol, and methyl isocyanate instead of trimethylsilyl isocyanate as white solids (recrystallized from ethyl acetate).

mp: 153.8°–155.0° C.; IR (KBr) √: 3390, 2900, 1660, 1540, 1360, 1210, 1070, 960, 910 cm$^{-1}$; $^1$H NMR (DMSO-d$_6$) δ: 9.32 (s, 1H), 7.81(d, J=6 Hz, 2H), 7.54–7.46 (m, 2H), 7.30–7.13 (m, 6H), 5.12 (q, J=7 Hz, 1H), 4.59–4.51 (m, 1H), 4.43 (t, J=8 Hz, 1H), 4.10 (t, J=8 Hz, 1H), 2.99 (dd, J=6, 13.5 Hz, 1H), 2.79 (dd, J=7, 13.5 Hz, 1H), 2.63 (d, J=4 Hz, 3H), 1.37 (d, J=7 Hz, 3H).

Example 26

N-[4-[3-(4,5-Dihydro-4(R)-phenyloxazol-2-yl)pyridyl-5-yl]-3-butyn-2-yl]-N-hydroxyurea The title compound was prepared in a similar manner to that of Example 21 employing 5-bromonicotinoyl chloride hydrochloride instead of 3-bromobenzoyl chloride.

mp: amorphous; IR (KBr) √: 3000–3500, 2950, 1650, 1500, 1420, 1160 cm$^{-1}$; $^1$H NMR (DMSO-d$_6$) δ: 9.40 (s, 1H), 9.20 (s, 1H), 8.76 (s, 1H), 8.23 (s, 1H), 7.40–7.31 (m, 5H), 6.60 (s, 2H), 5.45 (t, J=9 Hz, 1H), 5.18 (dd, J=7, 13.5 Hz, 1H), 4.90 (t, J=9.5 Hz. 1H), 4.25 (t, J=8.4 Hz, 1H), 1.38 (d, J=6.6 Hz, 3H).

Example 27

N-[4-[3-(4,5-Dihydro-4(R)-phenyloxazol-2-yl)pyridyl-5-yl]-3-butyn-2-yl]-N-hydroxy-N'-methylurea The title compound was prepared in a similar manner to example 26 employing methyl isocyanate instead of trimethylsilyl isocyanate as white solids (recrystallized from ethyl acetate).

mp: amorphous; IR (KBr) √: 3000–3400, 2900, 1650, 1530, 1360, 1080 cm$^{-1}$; $^1$H NMR (DMSO-d$_6$) δ: 9.35 (s, 1H), 9.20 (d, J=2 Hz, 1H), 8.76 (d, J =2 Hz, 1H), 8.22 (s, 1H), 7.38–7.31 (m, 5H), 7.14–7.13 (m, 1H), 5.46 (t, J=8.8 Hz, 1H), 5.17–5.14 (m, 1H), 4.90 (t, J=8.8 Hz, 1H), 4.25 (t, J=8.4 Hz 1H), 2.62 (d, J=4.7 Hz, 3H), 1.38 (d, J=6.8 Hz, 3H).

Example 28

(−)-N-1-[2-[3-(4,5-dihydro-4(R)-phenyloxazol-2-yl)phenoxy]ethyl]-N-hydroxyurea

A. 2-(3-benzyloxybenzamido)-2 (R)-phenylethan-1-ol

To a solution of 3-benzyloxybenzoic acid (22 g, 96 mmol) in toluene (200 ml) was added dropwise thionyl chloride (14.1 ml, 19 mmol). The reaction mixture was heated at 90° C. for 2 hours, cooled to ambient temperature and volatiles removed under reduced pressure to afford crude 3-benzyloxybenzoyl chloride (32 g, quant.). The crude 3-benzyloxybenzoyl chloride was dissolved in CH$_2$Cl$_2$ and added dropwise over 30 min., to a vigorously stirred solution of (R)-(−)-2-phenylglycinol (15.8 g, 115 mmol) and triethylamine (16 ml, 15 mmol) in CH$_2$Cl$_2$ (200 ml) cooled to 0° C. The reaction mixture was allowed to warm ambient temperature and stirred for overnight. Solvent was removed under reduced pressure and the residue partitioned between ethyl acetate (1 L) and water (1 L). The aqueous layer was separated, extracted with ethyl acetate (2×500ml) and the combined organic phase washed with 1N HCl (500 ml), aqueous 4% NaHCO$_3$ solution (500 ml) and brine (500 ml), dried over MgSO$_4$ and concentrated under reduced pressure to give 2-(3-benzyloxybenzamido)-2(R)-phenylethan-1-ol (29 g, 88%) as pale yellow solids.

$_1$H NMR (CDCl$_3$) δ: 7.46–7.29(m, 9H), 7.04–7.01(m, 1H), 5.34(t, J=8.8 Hz, 1H), 4.89–4.79(m, 1H), 4.31(t, J=8 Hz, 1H).

B. 2-(3-Benzyloxyphenyl)-4,5-dihydro-4(R)-phenyloxazole

To a mixture of 2-(3-benzyloxybenzamido)-2(R)-phenylethan-1-ol (29 g, 83 mmol) and triphenylphosphine (28.4 g, 108 mmol) in dry tetrahydrofuran (200 ml) was added dropwise a solution of diisopropyl azodicarboxylate (19.6 ml, 108 mmol) in dry tetrahydrofuran (30 ml). The reaction mixture was stirred for 4 hours and volatiles removed by evaporation. The residue was purified by column chromatography on silica gel eluting with ethyl acetate-hexane (=1:9) to afford 2-(3-benzyloxyphenyl)-4,5-dihydro-4(R)-phenyloxazole (23.5 g, 85%) as pale yellow solids.

$^1$H NMR (CDCl$_3$) δ: 7.70–7.63 (m, 2H), 7.46–7.28 (m, 11H), 7.15–7.11 (m, 1H), 5.39 (dd, J=8, 9.9 Hz, 1H), 5.11 (s, 2H), 4.80 (dd, J=8.4, 9.9 Hz, 1H), 4.27 (t, J=8 Hz, 1H).

C. 4,5-Dihydro-2-(3-hydroxyphenyl)-4(R)-phenyloxazole 2-(3-Benzyloxyphenyl)-4,5-dihydro-4(R)-phenyloxazole (3 g, 8.9 mmol) was dissolved in ethyl acetate (15 ml) and hydrogenolyzed in the presence of 10% palladium-on-charcoal (300 mg). Recrystallization from ethyl acetate/n-hexane gave 4,5-dihydro-2-(3-hydroxyphenyl)-4(R)-phenyloxazole (1.03 g, 48% ) as colorless needles.

$^1$H NMR (CDCl$_3$) δ: 7.56–7.53 (m, 2H), 7.38–7.28 (m, 6H), 6.98–6.95 (m, 1H), 6.37 (br. s, 1H), 5.38 (dd, J=8, 9.9 Hz, 1H), 4.80 (dd, J=8.4, 9.9 Hz, 1H), 4.29 (t, J=8 Hz, 1H).

D. 1-(tert-Butyldimethylsilyloxy)-2-[3- (4,5-dihydro-4 (R)-phenyloxazol-2-yl)-phenoxy]ethane To a stirred solution of 4,5-dihydro-2-(3-hydroxyphenyl)-4(R)-phenyloxazole (3.3 g, 13.8 mmol) in N,N-dimethylformamide (30 ml) was added sodium hydride (60% in mineral oil, 0.62 g, 16 mmol) portionwise over 5 min. at ambient temperature. The mixture was stirred for 1 hour, and then a solution of 2-bromo-1-(tert-butyldimethylsilyloxy)ethane (4.94 g, 21 mmol) in N,N-dimethylformamide (5 ml) was added dropwise over 5 min. and the reaction mixture stayed overnight. The reaction mixture was partitioned between ethyl acetate (50 ml) and water (50 ml), the aqueous layer was separated, extracted with ethyl acetate (2×50 ml) and the combined organic phase washed with 1N HCl (100 ml), aqueous 4% NaHCO$_3$ solution (100 ml) and brine (100 ml), dried (MgSO$_4$) and evaporated. The resulting residue was purified by column chromatography on silica gel eluting with ethyl acetate/n-hexane (=1:6) to afford 1-(tert-butyldimethylsilyloxy)-2-[3-(4,5-dihydro-4(R)-phenyloxazol-2-yl)phenoxy]ethane (4.7 g, 86%) as a colorless oil.

$^1$H NMR (CDCl$_3$) δ: 7.54–7.48 (m, 2H), 7.29–7.15 (m, 6H), 6.99–6.95 (m, 1H), 5.28 (dd, J=8, 9.9 Hz, 1H), 4.69 (dd, J=8.4, 9.9 Hz, 1H), 4.16 (t, J=8 Hz, 1H), 4.01–3.97 (m, 2H), 3.89–3.85 (m, 2H), 0.80 (s, 9H), 0.01 (s, 6H).

E. 2-[3-(4,5-Dihydro-4(R)-phenyloxazol-2-yl)phenoxy]ethan-1-ol

To a solution of 1-(tert-butyldimethylsilyloxy)-2-[3-(4,5-dihydro-4(R)-phenyloxazol-2-yl)phenoxy]ethane (4.4 g, 11 mmol) in THF (35 ml) was added dropwise tetrabutylammonium fluoride (1M in THF, 14 ml). The reaction mixture was stirred at room temperature for 45 min., solvent removed by evaporation and the resulting residue was purified by column chromatography on silica gel eluting with ethyl acetate/n-hexane (=1:2) to afford 2-[3-(4,5-dihydro-4(R)-phenyl-oxazol-2-yl)phenoxy]ethan-1-ol (2.8 g, 91%) as a colorless oil.

$^1$H NMR (CDCl$_3$) δ: 7.66–7.60 (m, 2H), 7.39–7.29 (m, 6H), 7.10–7.07 (m, 1H), 5.34 (dd, J=8, 10 Hz, 1H), 4.80 (dd, J=8.4, 10 Hz, 1H), 4.28 (t, J=8.4 Hz, 1H), 4.14 (t, J=4.4 Hz, 2H), 3.96 (br. s, 2H), 2.04 (br s, 1H).

F. (−)-N-1-[2-[3-(4,5-Dihydro-4(R)-phenyloxazol-2-yl)phenoxy]ethyl]-N-hydroxyurea 2-[3-(4,5-Dihydro-4(R)-phenyloxazol-2-yl)phenoxy]ethan-1-ol was elaborated to the title compound in a similar manner as described in Example 10 as colourless solids (recrystallized from ethyl acetate/hexane).

mp: 135.7°–137.4° C.; IR (KBr )ν: 3500, 3400, 2900, 1640, 1580, 1220, 1060, 990 cm$^{-1}$; $^1$H NMR (DMSO-d$_6$) δ: 9.45 (d, J=1.1 Hz, 1H), 7.54–7.29 (m, 8H), 7.18–7.15 (m, 1H), 6.37 (s, 2H), 5.41 (t, J=9 Hz, 1H), 4.85 (t, J=10 Hz, 1H), 4.23–4.14 (m, 3H), 3.72 (t, J=5.5 Hz, 2H). [α]$_D$:=−1° (c=0.2, methanol).

Elemental analysis:
Calc: C: 63.33%; H: 5.61%; N: 12.31%
Found: C; 63.29%; H: 5.54%; N: 12.27%

Example 29
N-1-[3-[3-(4,5-Dihydro-4(R)-phenyloxazol-2-yl)phenoxy]propyl]-N-hydroxyurea The titled compound was prepared in a similar manner to example 28 employing 3-bromo-1-(tert-butyldimethylsilyloxy)propane instead of 2-bromo-1-(tert-butyl-dimethylsilyloxy)ethane as white solids (recrystallized from ethyl acetate/hexane).

mp: 149.5°–150.8° C.; IR (KBr) ν: 3500, 3350, 3200, 1640, 1580, 1450, 1100, 980 cm$^{-1}$; $^1$H NMR (DMSO-d$_6$) δ: 9.29 (s, 1H), 7.52 (d, J=7.7 Hz, 1H), 7.44–7.28 (m, 7H), 7.16–7.12 (m, 1H), 6.29 (s, 2H), 5.40 (dd, J=8.4, 10 Hz, 1H), 4.84 (dd, J=8.4, 10 Hz, 1H), 4.19 (t, J=8.4 Hz, 1H), 4.05 (t, J=6.6 Hz, 2H), 3.49 (t, J=7 Hz, 2H), 1.98–1.93 (m, 2H).

Example 30
N-1-[2-[3-(4,5-Dihydro-4(R)-phenyloxazol-2-yl)phenoxy]ethyl]-N-hydroxy-N'-methylurea The titled compound was prepared in a similar manner to example 28 employing methyl isocyanate instead of trimethylsilyl isocyanate as white solids (recrystallized from ethyl acetate/hexane).

mp: 132.5°–133.6° C.; IR (KBr)ν: 3390, 3100, 2900, 1660, 1530, 1450, 1320, 1090, 1000, 950 cm$^{-1}$; $^1$H NMR (DMSO-d$_6$) δ: 9.39 (s, 1H), 7.54–7.29 (m, 8H), 7.17–7.14 (m, 1H), 6.93–6.92 (m, 1H), 5.41 (t, J=8 Hz, 1H), 4.84 (dd, J=8.4, 10 Hz, 1H), 4.34–4.13 (m, 3H), 3.71 (t, J=5.5 Hz, 2H), 2.60 (d, J=5 Hz, 3H).

Example 31
(+)-N-1-[2-[3-(4,5-Dihydro-4(R)-phenyloxazol-2-yl)-5-fluorophenoxy]ethyl]-N-hydroxyurea The titled compound was prepared in a similar manner to example 28 employing 3-benzyloxy-5-fluorobenzoic acid instead of 3-benzyloxybenzoic acid as white solids (recrystallized from ethyl acetate/hexane).

mp: 122.4°–123.7° C.; IR (KBr)ν: 3500, 3400, 3200, 1660, 1580, 1440, 1150, 1030, 930 cm$^{-1}$; $^1$H NMR (DMSO-d$_6$) δ: 9.45 (s, 1H), 7.40–7.25 (m, 7H), 7.12–7.07 (m, 1H), 6.38 (s, 2H), 5.42 (dd, J=8.4, 9.9 Hz, 1H), 4.86 (dd, J=8.4, 9.9 Hz, 1H), 4.25–4.16 (m, 3H), 3.70 (t, J=5.5 Hz, 2H). [α]$_D$:=+3.5° (c=0.2, methanol).

Example 32
(+)-N-1-[2-[3-[4,5-Dihydro-4(R)-(4-fluorophenyl)oxazol-2-yl]phenoxy]ethyl]-N-hydroxyurea The titled compound was prepared in a similar manner to example 28 employing (R)-(−)-2-(4-fluorophenyl)glycinol instead of (R)-(−)-2-phenylglycinol as white solids (recrystallized from methanol/ethyl acetate).

mp: 150.3°–151.9° C.; IR (KBr)ν: 3500, 3320, 2900, 1630, 1510, 1210, 1070, 990 cm$^{-1}$; $^1$H NMR (DMSO-d$_6$) δ: 9.45 (s, 1H), 7.52 (d, J=7.7 Hz, 1H), 7.45–7.32 (m, 4H), 7.22–7.16 (m, 3H), 6.38 (s, 2H), 5.42 (t, J=9.2 Hz, 1H), 4.84 (t, J=9.2 Hz, 1H), 4.21–4.13 (m, 3H), 3.71 (t, J=6 Hz, 2H). [α]$_D$:=+0.5° (c=0.2, methanol).

Example 33
N-1-[2(R)-[3-(4,5-Dihydro-4(R)-phenyloxazol-2-yl)phenoxy]propyl]-N-hydroxyurea A. 1-(tert-Butyldimethylsilyloxy)-2(R)-[3-(4,5-dihydro-4(R)-phenyloxazol-2-yl)phenoxy]propane To a mixture of 4,5-dihydro-2-(3-hydroxyphenyl)-4(R)-phenyloxazole (5.0 g, 20.9 mmol), 1-(tert-butyldimethylsilyloxy)propan-2(S)-ol (4.76 g, 25 mmol) and triphenylphosphine (6.58 g, 25 mmol) in dry tetrahydrofuran (30 ml) was added dropwise a solution of diethyl azodicarboxylate (3.9 ml, 25 mmol) in dry tetra-hydrofuran (5 ml). The reaction mixture was stirred ambient temperature for 1 h and then ay 50° C. for 5 hours. Volatiles were removed by evaporation and the resulting residue purified by column chromatography on silica gel eluting with ethyl acetate-hexane (=1:6) to afford 1-(tert-butyldimethylsilyloxy)-2(R)-[3-(4,5-dihydro-4(R)-phenyloxazol-2-yl)phenoxy]propane (8.7 g, quant.) as a colorless oil.

$^1$H NMR (CDCl$_3$) δ: 7.62–7.59 (m, 2H), 7.38–7.29 (m, 6H), 7.08–7.05 (m, 1H), 5.38 (t, J=10 Hz, 1H), 4.78 (dd, J=8.4, 10 Hz, 1H), 4.55–4.8 (m, 1H), 4.26 (t, J=8 Hz, 1H), 3.80 (dd, J=5.9, 10.6 Hz, 1H), 3.65 (dd, J=5.1, 10.6 Hz, 1H), 1.57 (d, J=8 Hz, 3H), 0.88 (s, 9H), 0.06 (s, 3H), 0.04 (s, 3H).

B. N-1-[2(R)-[3-(4,5-Dihydro-4(R)-phenyloxazol-2-yl)phenoxy]propyl]-N-hydroxyurea The titled compound was prepared in a similar manner to example 28 employing 1-(tert-butyldimethylsilyloxy)-2(R)-[3-(4,5-dihydro-4(R)-phenyloxazol-2-yl)phenoxy]propane instead of 1-(tert-butyldimethylsilyloxy)-2-[3-(4,5-dihydro-4(R)-phenyloxazol-2-yl)phenoxy]ethane as amorphous.

IR (Nujol) ν: 3200, 2900, 1650, 1580, 1450, 980 cm$^{-1}$; $^1$H NMR (DMSO-d$_6$) δ: 9.47 (s, 1H), 7.52–7.28 (m, 8H), 7.16 (d, J=8 Hz, 1H), 6.31 (s, 2H), 5.40 (t, J=8.4 Hz, 1H), 4.84 (t, J=8.8 Hz, 1H), 4.72–4.66 (m, 1H), 4.19 (t, J=8.4 Hz, 1H), 3.71 (dd, J=6, 14 Hz, 1H), 3.38 (dd, J=6, 14 Hz, 1H), 1.25 (d, J=6 Hz, 3H).

Elemental analysis:
Calc: C: 63.32%; H: 5.96%; N: 11.82%
Found: C: 63.11%; H: 6.11%; N: 11.47%

Example 34
N-1-[2(S)-[3-(4,5-Dihydro-4(R)-phenyloxazol-2-yl)phenoxy]propyl]-N-hydroxyurea The titled compound was prepared in a similar manner to example 28 employing 1-(tert-butyldimethylsilyloxy)-2(S)-[3-(4,5-dihydro-4(R)-phenyloxazol-2-yl)phenoxy]propane instead of 1-(tert-butyldimethylsilyloxy)-2-[3-(4,5-dihydro-4(R)-phenyloxazol-2-yl)phenoxy]ethane as white solids (recrystallized from ethyl acetate/hexane).

mp: 163.4°–164.7° C.; IR (Nujol) ν: 3450, 3200, 2850, 1620, 1580, 1450, 1210, 1080, 980 cm$^{-1}$; $^1$H NMR (DMSO-d$_6$) δ: 9.47 (s, 1H), 7.53–7.14 (m, 9H), 6.32(s, 2H), 5.40 (t, J=9.9 Hz, 1H), 4.84 (t, J=8.4 Hz, 1H), 4.70 (q, J=5.8 Hz, 1H), 4.19 (t, J=8.4 Hz, 1H), 3.70 (dd, J=6, 14 Hz, 1H), 3.41 (dd, J=6, 14 Hz, 1H), 1.26 (d, J=6 Hz, 3H).

Elemental analysis:
Calc: C: 63.32%; H: 5.96%; N: 11.82%
Found: C: 64.42%; H: 6.09%; N: 11.80%

Example 35
(+)-N-1-[2-[3-[4,5-Dihydro-4(S)-phenyloxazol-2-yl]phenoxy]ethyl]-N-hydroxyurea A: 4,5-Dihydro-2-(3-hydroxyphenyl)-4(S)-phenyloxazole 4,5-Dihydro-2-(3-hydroxyphenyl)-4(S)-phenyloxazole was prepared in a similar manner to example 28° C. employing (S)-(+)-phenylglycinol instead of (R)-(−)-phenylglycinol.

$^1$H-NMR (CDCl$_3$+2 drops DMSO-d$_6$)δ: 8.8 (s, 1H), 7.53–7.50 (m, 2H), 7.36–7.18 (m, 6H), 7.00 (d, J=7 Hz, 1H), 5.33 (t, J=8 Hz, 1H), 4.77 (t, J=10 Hz, 1H), 4.24 (t, J=8 Hz, 1H).

B: Ethyl 3-(4,5-dihydro-4(S)-phenyloxazol-2-yl) phenoxyacetate

To a vigorously stirred mixture of 4,5-dihydro-2-(3-hydroxyphenyl)-4(S)-phenyloxazole (2.04 g, 8.5 mmol) and potassium carbonate (2.36 g, 17 mmol) in DMF (40 ml) was added dropwise over 5 min. a solution of ethyl bromoacetate (1.71 g, 10.2 mmol) in DMF (5 ml) at ambient temperature. The reaction mixture was stirred for 12 h and then poured into water (100 ml). The mixture was extracted with diethyl ether (3×50 ml), and the combined extracts were washed with brine (50 ml), dried ($MgSO_4$) and concentrated under reduced pressure to afford title compound (2.77 g, quant.) as a pale yellow liquid.

$^1$H-NMR ($CDCl_3$)δ: 7.68 (d, J=7 Hz, 1H), 7.57 (d, J=2 Hz, 1H), 7.39–7.28 (m, 6H), 7.12 (dd, J=7 and 2 Hz, 1H), 5.38 (dd, J=8 and 10 Hz, 1H), 4.79 (t, J=8 Hz, 1H), 4.67 (s, 2H), 4.31–4.23 (m, 3H), 1.29 (t, J=7 Hz, 3H).

C: 2-[3-[4,5-Dihydro-4(S)-phenyloxazol-2-yl]phenoxy] ethan-1-ol

To a THF (40 ml) solution of ethyl 3-(4,5-dihydro-4(S)-phenyloxazol-2-yl)phenoxyacetate (2.77 g, 8.5 mmol) was added $LiBH_4$ (0.37 g, 17 mmol) in one portion. After stirring for 4 h, water (40 ml) was added and the mixture diluted with diethyl ether (40 ml). The aqueous layer was separated and extracted with ethyl acetate (3×20 ml). The combined organic extracts were washed with 0.5 N aqueous HCl (20 ml), brine (20 ml), dried ($MgSO_4$) and concentrated under reduced pressure. The crude product was purified by column chromatography on silica gel eluting with hexane/ethyl acetate (=2:1) to afford title compound (0.95 g, 40%) as a colorless liquid.

$^1$H-NMR ($CDCl_3$) δ: 7.66–7.59 (m, 2H), 7.39–7.26(m, 6H), 7.06 (dd, J=2 and 7 Hz, 1H), 5.39 (dd, J=10 and 8 Hz, 1H), 4.80 (dd, J=10 and 8 Hz, 1H), 4.28 (t, J=8 Hz, 1H), 4.16–4.12 (m, 2H), 3.98–3.92 (m, 2H), 2.18 (br s, 1H).

D: (+)-N-1-[2-[3-[4,5-Dihydro-4(S)-phenyloxazol-2-yl] phenoxy]ethyl]-N-hydroxyurea 2-[3-[4,5-Dihydro-4(S)-phenyloxazol-2-yl]phenoxy] ethan-1-ol was elaborated to the title compound in an analogous manner as described in example 28 F. It was recrystallized from ethyl acetate to give a white solid.

mp: 146.5°–147.1° C.; IR (KBr) ν́: 3490, 3320, 2875, 1630, 1590, 1580, 1220, 700 $cm^{-1}$; $^1$H-NMR (DMSO-$d_6$) δ: 9.47 (s, 1H), 7.52 (d, J=8 Hz, 1H), 7.45–7.25 (m, 7H), 7.16 (dd, J=8 and 2 Hz, 1H), 6.40 (s, 2H), 5.41 (t, J=10 Hz, 1H), 4.85 (t, J=8.5 Hz, 1H), 4.23–4.13 (m, 3H), 3.71 (t, J=5.5 Hz, 2H). $[α]_D$:=+7.65° (c=0.2, methanol)

Elemental analysis:
Calc. C: 63.33%; H: 5.61%; N: 12.31%
Found. C: 62.83%; H: 5.60%; N: 12.24%

Example 36

N-1-[2-[3-[4,5-Dihydro-4(R)-phenyloxazol-2-yl]-2-fluorophenoxy]ethyl]-N-hydroxyurea N-1-[2-[3-[4,5-Dihydro-4(R)-phenyloxazol-2-yl]-2-fluorophenoxy]ethyl]-N-hydroxy urea was prepared in a similar manner as described for example 35 employing 4,5-dihydro-2-(2-fluoro-3-hydroxyphenyl)-4(R)-phenyloxazol e instead of 4,5-dihydro-2-(3-hydroxyphenyl)-4(S)-phenyloxazole. white solid (amorphous)

IR (KBr) ν́: 3500, 3320, 2800, 1630, 1590, 700 $cm^{-1}$; $^1$H-NMR (DMSO-$d_6$)δ: 9.51 (s, 1H), 7.45–7.20 (m, 8H), 6.40 (s, 2H), 5.42 (t, J=9 Hz, 1H), 4.81 (t, J=9 Hz, 1H), 4.30–4.10 (m, 3H), 3.80–3.70 (br s, 2H).

Elemental analysis:
Calc. C:60.16%; H: 5.05%; N: 11.69%
Found. C:57.92%; H: 5.10%; N: 11.36%

The starting material 4,5-dihydro-2-(2-fluoro-3-hydroxyphenyl)-4(R)-phenyloxazole was prepared as follows.

A: 3-tert-Butyldimethylsilyloxy-2-fluorophenol

To a solution of 2-fluorophenol (10.35 g, 9.2 mmol) and tert-butyldimethylsilyl chloride (101 mmol) in DMF (180 ml) was added imidazole (7.54 g, 110 mmol) in one portion. After stirring for 3 h the reaction mixture was poured into water (300 ml) and extracted with diethyl ether (3×100 ml). The combined extracts were washed with 10% aqueous citric acid (100 ml), brine (100 ml), dried ($MgSO_4$) and concentrated under reduced pressure to afford title compound (20.63 g, quant.) as a colorless liquid.

$^1$H-NMR ($CDCl_3$) δ: 7.10–6.84 (m, 4H), 0.98 (s, 9H), 0.20 (s, 6H).

B: 3-tert-Butyldimethylsilyloxy-2-fluorobenzoic acid

A solution of 3-tert-butyldimethylsilyloxy-2-fluorophenol (10.59 g, 46.8 mmol) in THF (150 ml) cooled to −70° C. was added dropwise over 5 min. sec-butyllithium (42 ml, 1.12M in cyclohexane). The reaction mixture was stirred ad −70° C. for 1 h and then poured into a slurry of dry-ice/diethyl ether. Water (200 ml) was added cautiously and the organic layer separated and discarded. The aqueous layer was acidified to pH 2 with concentrated HCl and extracted with ethyl acetate (3×100 ml). The combined organic extracts were dried ($MgSO_4$) and evaporated to afford title compound (7.90 g, 70%) as a white solid.

$^1$H-NMR (DMSO-$d_6$) δ: 7.45–7.37 (m, 1H), 7.25–7.11 (m, 2H), 0.98 (s, 9H), 0.20 (s, 6H).

C: Benzyl 3-benzyloxy-2-fluorobenzoate

To a mixture of 3-tert-butyldimethylsilyloxy-2-fluorobenzoic acid (7.74 g, 29 mmol), potassium carbonate (24.0 g, 174 mmol) and sodium iodide (25.9 g, 174 mmol) in DMF (180 ml) was added benzyl chloride (8.33 ml, 72.4 mmol) dropwise over 5 min. After stirring for 2 days the reaction mixture was poured into water (400 ml) and extracted with diethyl ether (3×200 ml). The combined extracts were washed with brine (100 ml), dried ($MgSO_4$) and concentrated under reduced pressure. The crude product obtained was recrystallized from 2-propanol to afford title compound (7.19 g, 74%) as white flakes.

$^1$H-NMR ($CDCl_3$) δ: 7.51–7.32 (m, 11H), 7.16 (t, J=7 Hz, 1H), 7.05 (t, J=7 Hz, 1H), 5.38 (s, 2H), 5.15 (s, 2H).

D: 3-Benzyloxy-2-fluorobenzoic acid

To a solution of benzyl 3-benzyloxy-2-fluorobenzoate (7.13 g, 21 mmol) in methanol (40 ml) was added an aqueous solution of potassium hydroxide (2.38 g, 42 mmol in 40 ml of water) and the mixture heated at reflux for 30 min. The reaction mixture was cooled, washed with diethyl ether (20 ml) and the ethereal layer was discarded. The aqueous layer was acidified to pH 2 with concentrated HCl and extracted with ethyl acetate (3×40 ml). The combined organic extracts were washed with brine (20 ml), dried ($MgSO_4$) and evaporated to afford title compound (4.83 g, 85%) as white solids.

$^1$H-NMR (DMSO-$d_6$) δ: 13.2 (br s, 1H), 7.50–7.30 (m, 7H), 7.18 (t, J=7 Hz, 1H), 5.21 (s, 2H).

E: 4,5-Dihydro-2-(2-fluoro-3-hydroxyphenyl)-4(R)-phenyloxazole

3-Benzyloxy-2-fluorobenzoic acid was elaborated to the title compound in a similar manner as described in example 28.

$^1$H-NMR ($CDCl_3$+1 drop DMSO-$d_6$) δ: 8.40 (br s, 1H), 7.45–7.18 (m, 6H), 7.10 (t, J=8 Hz, 1H), 7.02 (t, J=8 Hz, 1H), 5.39 (t, J=8 Hz, 1H 4.75 (t, J=8 Hz, 1H), 4.22 (t, J=8 Hz, 1H).

Example 37
(−)-N-1-[2-[3-[4,5-Dihydro-5(R)-phenyloxazol-2-yl]-2-fluorophenoxy]ethyl]-N-hydroxyurea A: 2-(3-tert-Butyldimethylsilyloxy-2-fluorobenzamido)-1(S)-phenylethanol To a solution of 3-tert-butyldimethylsilyloxy-2-fluorobenzoic acid (3.3 g, 12 mmol, example 36B) in toluene (30 ml) was added thionyl chloride (1.3 ml, 18 mmol) carefully at ambient temperature. After addition was complete, the reaction mixture was heated at reflux for 40 min, then cooled and concentrated in vacuo. The residual oil was dissolved in $CH_2Cl_2$ (20 ml) and added dropwise to a solution of (+)-2-amino-1(S)-phenylethanol (1.7 g, 12 mmol, see A. I. Meyers and J. Slade. *J. Org. Chem.* 1980, 45, 2785.) and triethylamine (2.0 ml, 15 mmol) in $CH_2Cl_2$ (20 ml) cooled to 0° C. The reaction mixture was allowed to warm to ambient temperature and stirred a further 30 min. The mixture was poured into water (100 ml) and extracted with $CH_2Cl_2$ (3×10 ml). The combined organic extracts were washed with saturated aqueous $NaHCO_3$ (100 ml), dried ($MgSO_4$) and concentrated under reduced pressure. The crude product was purified by column chromatography on silica gel eluting with hexane/ethyl acetate (=3:2) to afford title compound (4.6 g, 97%) as a pale yellow liquid.

$^1$H-NMR (CDCl$_3$) δ: 7.70–7.01 (m, 8H), 5.00 (m, 1H), 4.00–3.85 (m, 1H), 3.70–3.55 (m, 1H), 3.25 (br s, 1H), 1.02 (s, 9H), 0.22 (s, 6H).

B: 2-(3-tert-Butyldimethylsilyloxy-2-fluorophenyl)-4,5-dihydro-5(R)-phenyloxazole To a solution of 2-(3-tert-butyldimethylsilyloxy-2-fluorobenzamido)-1(S)-phenylethanol (4.6 g, 12 mmol) and triphenylphosphine (3.7 g, 14 mmol) in THF (50 ml) was added dropwise a solution of diethyl azodicarboxylate (2.2 ml, 42 mmol) in THF (20 ml). After stirring for 1 h, volatiles were removed by evaporation. The residue was purified by column chromatography on silica gel eluting with hexane-ethyl acetate (13:1 to 9:1) to afford the title compound (2.2 g, 50%) as a pale yellow liquid.

$^1$H-NMR (CDCl$_3$) δ: 7.60–6.98 (m, 8H), 5.63 (dd, J=10 and 8 Hz, 1H), 4.53 (dd, J=15.0 and 8 Hz, 1H), 1.01 (s, 9H), 0.21(s, 6H).

C: 4,5-Dihydro-2-(2-fluoro-3-hydroxyphenyl)-5(R)-phenyloxazole

To a solution of 2-(3-tert-butyldimethylsilyloxy-2-fluorophenyl)-4,5-dihydro-5(R)-phenyloxazole (2.2 g, 5.8 mmol) in THF (20 ml) was added dropwise tetrabutylammonium fluoride (1M in THF, 7 ml). The reaction mixture was stirred at ambient temperature for 10 min., volatiles removed by evaporation and the resulting residue was purified by column chromatography on silica gel eluting with hexane-ethyl acetate (3:2) to afford the title compound (1.3 g, 86%) as colorless solids.

$^1$H-NMR (CDCl$_3$) δ: 10.70–9.50 (br, 1H), 7.58–7.03 (m, 8H), 5.74 (m, 1H), 4.43 (m, 1H), 3.78 (m, 1H).

D: 2-[3-(4,5-Dihydro-5(R)-phenyloxazol-2-yl)-2-fluorophenoxy]ethyl methacrylate

To a solution of 4,5-dihydro-2-(2-fluoro-3-hydroxyphenyl)-5(R)-phenyloxazol e (0.97 g, 3.8 mmol), triphenylphosphine (1.0 g, 4.0 mmol) and 2-hydroxyethyl methacrylate (0.50 ml, 4.0 mmol) in THF (30 ml) was added dropwise a solution of diethyl azodicarboxylate (0.65 ml, 4.0 mmol) in THF (15 ml). After stirring for 1 day, volatiles were removed by evaporation. The residue was purified by column chromatography on silica gel eluting with hexane-ethyl acetate (2:1) to afford the title compound (1.2 g, 86%) as a pale yellow liquid.

$^1$H-NMR (CDCl$_3$) δ: 7.58–7.00 (m, 8H, m), 6.15 (dd, J=4.4 and 3.7 Hz, 1H), 4.58–4.45 (m, 2H), 4.32 (m, 2H), 4.08 (dd, J=15.0 and 7.7 Hz, 1H), 3.85 (t , J=4.8 Hz, 1H), 1.94 (t, J=3.3 Hz, 3H).

E: 2-[3-[4,5-Dihydro-5(R)-phenyloxazol-2-yl]-2-fluorophenoxy]ethan-1-ol

To a solution of 2-[3-(4,5-dihydro-5(R)-phenyloxazol-2-yl)-2-fluorophenoxy] ethyl methacrylate, (1.2 g, 3.3 mmol) in THF (40 ml) and water (50 ml) was added lithium hydroxide monohydrate (0.41 g, 9.8 mmol). After stirring for 2 h, the mixture was extracted with ethyl acetate (3×50 ml) and the combined organic extracts were washed with saturated aqueous $NaHCO_3$ (30 ml), brine (30 ml), dried ($MgSO_4$) and concentrated in vacuo. The residue was purified by column chromatography on silica gel eluting with hexane-ethyl acetate (1:2) to afford the title compound (0.76 g, 78%) as a colorless liquid.

$^1$H-NMR (CDCl$_3$) δ: 7.70–7.02 (m, 8H), 5.68 (dd, J=10 and 8 Hz, 1H), 4.55 (dd, J=10 and 15.0 Hz, 1H), 4.19 (t, J=4.4 Hz, 2H), 4.10 (dd, J=8.1 Hz, 1H), 4.02 (t, J=3.7 Hz, 2H), 2.54 (br s, 1H).

F: N,O-Di(tert-butoxycarbonyl)-2-[3-(4,5-dihydro-5(R)-phenyloxazol-2-yl)-2-fluorophenoxy]ethyl hydroxylamine 2-{3-[4,5-Dihydro-5(R)-phenyloxazol-2-yl]-2-fluorophenoxy} ethan-1-ol was elaborated to the title compound in a similar manner as described in Example 10 C.

$^1$H-NMR (CDCl$_3$) δ: 7.70–7.04 (m, 8H), 5.69 (m, 1H), 4.54 (m, 1H), 4.40–4.22 (m, 2H), 4.20–3.90 (m, 3H), 1.58 (s, 18H).

G: (−)-N-1-[2-[3-[4,5-Dihydro-5(R)-phenyloxazol-2-yl]-2-fluorophenoxy]ethyl]-N-hydroxyurea N,O-Di(tert-butoxycarbonyl)-2-[3-(4,5-dihydro-5(R)-phenyloxazol-2-yl)-2-fluoro phenoxy]ethyl hydroxylamine was elaborated to the title compound in a similar manner as described in Example 1 D. It was recrystallized from ethyl acetate to give a colorless solid.

mp: 107°–108° C.; IR (KBr) ѵ: 3400, 1740, 1650, 1360, 1050, 740 cm$^{-1}$; $^1$H-NMR (DMSO-d$_6$) δ: 9.50 (s, 1H), 7.60–7.15 (m, 8H), 6.38 (s, 2H), 5.79 (t, J=10 Hz, 1H), 4.45 (t, J=10 Hz, 1H), 4.23 (m, 2H), 3.83 (dd, J=15 and 8 Hz, 1H), 3.75 (t, J=5.5 Hz, 18H). [α]$_D$:=−71.4 (c=0.098, methanol)

Elemental analysis:
Calc. C: 60.16%; H: 5.05%; N: 11.69%
Found. C: 59.67%; H: 5.36%; N: 10.77%

Example 38
(+)-N-1-[2-[3-[4,5-Dihydro-5(S)-phenyloxazol-2-yl]-2-fluorophenoxy]ethyl]-N-hydroxyurea The title compound was prepared in a similar manner to example 37 employing (−)-2-amino-1(R)-phenylethanol (A. I. Meyers and J. Slade. *J. Org. Chem.* 1980, 45, 2785) instead of (+)-2-amino-1(S)-phenylethanol. It was recrystallized from ethyl acetate to give a white solid.

mp: 106°–107° C.; IR (KBr) ѵ: 3400, 1740, 1650, 1360, 1050, 720 cm$^{-1}$; $^1$H-NMR (DMSO-d$_6$) δ: 9.50 (s, 1H), 7.60–7.15 (m, 8H), 6.38 (s, 2H), 5.79 (t, J=10 Hz, 1H), 4.45 (t, J=10 Hz, 1H), 4.23 (m, 2H), 3.83 (dd, J=15 and 8 Hz, 1H), 3.75 (t, J=5.5 Hz, 18H). [α]$_D$:=+87.8 (c=0.11, methanol)

Elemental analysis:
Calc. C: 60.16%; H: 5.05%; N: 11.69%
Found. C: 59.57%; H: 5.35%; N: 10.71%

Example 39
(+)-N-1-[2-[5-Chloro-3-[4,5-dihydro-4(R)-phenyloxazol-2-yl]-2-fluorophenoxy]ethyl]-N-hydroxyurea The title compound was prepared in a similar manner to example 37 employing (R)-(−)-2-phenylglycinol instead of (−)-2-amino-1(R)-phenylethanol, and 4-chloro-2-fluorophenol instead of 2-fluorophenol.

mp: 71°–73° C.; IR (KBr) ν: 3500, 1650, 1580, 1500, 1360, 1280, 1050, 700 cm$^{-1}$; $^1$H-NMR (DMSO-d$_6$) δ: 7.51 (dd, J=7.0, 2.6 Hz, 1H), 7.48–7.23 (m, 6H), 6.36 (s, 2H), 5.41 (t, J=1.8 Hz, 1H), 4.81 (dd, J=10.3 and 8.4 Hz, 1H), 4.25 (t, J=5.5 Hz, 2H), 4.17 (t, J=8.4 Hz, 1H), 3.70 (t, J=5.5 Hz, 2H). [α]$_D$:=+7.0 (c=0.17, methanol)

Elemental analysis:
Calc. C: 54.90%; H: 4.35%; N: 10.67%
Found. C: 54.35%; H: 4.41%; N: 10.72%

Example 40

(+)-N-1-[2-[3-[4,5-dihydro-4(R)-phenyloxazol-2-yl]-2-fluoro-4-methylphenoxy]ethyl]-N-hydroxyurea The title compound was prepared in a similar manner to example 37 employing (R)-(–)-2-phenylglycinol instead of (–)-2-amino-1(R)-phenylethanol, and 2-fluoro-4-methylphenol instead of 2-fluorophenol.

mp: 53°–55° C.; IR (KBr) ν: 3500, 1650, 1500, 1370, 1280, 1150, 1060, 980, 750, 700 cm$^{-1}$; $^1$H-NMR (DMSO-d6) δ: 9.48 (s, 1H), 7.50–7.20 (m, 7H), 6.41 (s, 2H), 5.42 (m, 1H), 4.82 (m, 1H), 4.30–4.12 (m, 3H), 3.72 (t, J=5.5 Hz, 2H), 2.31 (s, 3H).

Elemental analysis:
Calc. C: 61.12%; H: 5.40%; N: 11.25%
Found. C: 59.85%; H: 5.43%; N: 11.11%

We claim:

1. A compound of the following chemical formula:

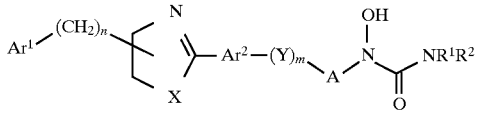

or a pharmaceutically acceptable salt or stereoisomer thereof, wherein
A is $C_1$–$C_4$ alkylene, CH(R), CH(R)CH$_2$ or CH(R)CH$_2$CH$_2$, in which R is methyl or ethyl;
m is one and n is zero or one;
R$^1$ and R$^2$ are each hydrogen, $C_1$–$C_4$ alkyl or $C_2$–$C_6$ alkenyl;
X is O or S;
Y is O, S, CH=CH or C≡C;
Ar$^1$ is phenyl or phenyl mono-substituted with halogen, $C_1$–$C_4$ alkyl, $C_1$–$C_4$ alkoxy, $C_1$–$C_4$ halo-substituted alkyl or $C_1$–$C_4$ halo-substituted alkoxy; and
Ar$^2$ is phenylene, pyridylene or phenylene mono- or di-substituted with halogen, $C_1$–$C_4$ alkyl, $C_1$–$C_4$ alkoxy, $C_1$C$_4$ halo-substituted alkyl or $C_1$–$C_4$ halo-substituted alkoxy.

2. A compound according to claim 1 wherein n is zero; R$^1$ is hydrogen; R$^2$ is hydrogen or methyl.

3. A compound according to claim 2 wherein R$^2$ is hydrogen; X is O; Ar$^1$ is phenyl or 4-fluorophenyl; and Ar$^2$ is 1,3-phenylene or 1,3-phenylene having one substituent selected from halogen, $C_1$–$C_4$ alkyl, $C_1$–$C_4$ alkoxy, $C_1$–$C_4$ halo-substituted alkyl and $C_1$–$C_4$ halo-substituted alkoxy.

4. A compound according to claim 3 wherein A is CH$_2$, CH$_2$CH$_2$, CH(CH$_3$) or CH(CH$_3$)CH$_2$; and Ar$^2$ is 1,3-phenylene or 1,3-phenylene having one fluoro substituent; m is one; and Y is O.

5. A compound according to claim 4, wherein Ar$^1$ is attached to the 4-position of the oxazoline ring and the carbon atom to which Ar$^1$ is attached has the (R)-configuration.

6. A compound according to claim 5 wherein the compound is selected from:
(–)-N-1-[2-[3-(4,5-dihydro-4(R)-phenyloxazol-2-yl)phenoxy]ethyl]-N-hydroxyurea;
(+)-N-1-[2-[3-(4,5-Dihydro-4(R)-phenyloxazol-2-yl)-5-fluorophenoxy]ethyl]-N-hydroxyurea; and
N-1-[2-[3-[4,5-Dihydro-4(R)-phenyloxazol-2-yl]-2-fluorophenoxy]ethyl]-N-hydroxyurea.

7. A compound according to claim 3 wherein A is CH$_2$ or CH(CH$_3$); m is one; and Y is C≡C.

8. A compound according to claim 7 wherein the compound is selected from:
(+)-N-[3-[3-(4,5-Dihydro-4(R)-phenyloxazol-2-yl)phenyl]-2-propyn-1-yl]-N-hydroxy-N'-methylurea;
(+)-N-[3-[3-[4,5-Dihydro-4(R)-(4-fluorophenyl)oxazol-2-yl]phenyl]-2-propyn-1-yl]-N-hydroxyurea;
(–)-N-[3-[3-(4,5-Dihydro-4(R)-phenyloxazol-2-yl)-2-fluorophenyl]-2-propyn-1-yl]-N-hydroxyurea; and
N-[4-[3-(4,5-Dihydro-5-phenyloxazol-2-yl)phenyl]-3-butyn-2-yl]-N-hydroxyurea.

9. A method for the treatment of a medical condition for which a 5-lipoxygenase inhibitor is needed, in a mammalian subject, which comprises administering to said subject a therapeutically effective amount of a compound according to claim 1.

10. A method according to claim 9, wherein the medical condition is an allergic or inflammatory condition.

11. A pharmaceutical composition for the treatment of an allergic or inflammatory condition in a mammalian subject which comprises a therapeutically effective amount of a compound of claim 1 and a pharmaceutically acceptable carrier.

* * * * *